(12) United States Patent
Nakagami et al.

(10) Patent No.: US 12,377,227 B2
(45) Date of Patent: *Aug. 5, 2025

(54) HEMOSTASIS VALVE-EQUIPPED INDWELLING NEEDLE AND INDWELLING NEEDLE ASSEMBLY

(71) Applicant: NIPRO CORPORATION, Osaka (JP)

(72) Inventors: Hiroyuki Nakagami, Osaka (JP); Shingo Sakamoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,770

(22) Filed: Sep. 26, 2023

(65) Prior Publication Data

US 2024/0009406 A1    Jan. 11, 2024

Related U.S. Application Data

(62) Division of application No. 16/635,219, filed as application No. PCT/JP2018/029139 on Aug. 2, 2018, now Pat. No. 11,839,752.

(30) Foreign Application Priority Data

Aug. 2, 2017  (JP) ................. 2017-150204
Nov. 9, 2017  (JP) ................. 2017-216744

(51) Int. Cl.
*A61M 5/38* (2006.01)
*A61M 5/158* (2006.01)
(Continued)

(52) U.S. Cl.
CPC ............ *A61M 5/385* (2013.01); *A61M 5/158* (2013.01); *A61M 5/165* (2013.01);
(Continued)

(58) Field of Classification Search
CPC ...... A61M 5/385; A61M 5/158; A61M 5/165; A61M 39/0693; A61M 39/06;
(Continued)

(56) References Cited

U.S. PATENT DOCUMENTS 5,290,246 A    3/1994  Yamamoto et al.
6,749,588 B1   6/2004  Howell et al.
(Continued)

FOREIGN PATENT DOCUMENTS

CN    101563044 A   10/2009
CN    102355923 A    2/2012
(Continued)

OTHER PUBLICATIONS

Nov. 2, 2023 Office Action issued in Japanese Patent Application No. 2023-001335.
(Continued)

*Primary Examiner* — Michael J Tsai
*Assistant Examiner* — Justin L Zamory
(74) *Attorney, Agent, or Firm* — Oliff PLC

(57) ABSTRACT

A novel hemostasis valve-equipped indwelling needle that is capable of discharging air in an internal flow path includes a cannula to be inserted percutaneously into a blood vessel on a distal end side thereof, a link connector on a proximal end side thereof, an internal flow path extending from the cannula to the link connector, and a hemostatic valve disposed inside the link connector. An air vent passage that allows the internal flow path to communicate with an external space is formed in the link connector further on the cannula side than the hemostatic valve, and a filter that allows gas to pass through but does not allow liquid to pass through is mounted in a compressed state on the air vent passage.

12 Claims, 10 Drawing Sheets

(51) Int. Cl.
*A61M 5/165* (2006.01)
*A61M 39/06* (2006.01)
*A61M 39/26* (2006.01)

(52) U.S. Cl.
CPC ........ *A61M 39/0693* (2013.01); *A61M 39/26* (2013.01); *A61M 2205/7536* (2013.01)

(58) Field of Classification Search
CPC ............ A61M 39/0613; A61M 39/045; A61M 39/26; A61M 2039/266; A61M 2039/062; A61M 2039/064; A61M 2039/066; A61M 2039/0673; A61M 2205/7536; A61M 25/0631; A61M 25/0625
See application file for complete search history.

(56) References Cited

U.S. PATENT DOCUMENTS

| | | | |
|---|---|---|---|
| 2010/0204648 A1* | 8/2010 | Stout ................. | A61M 39/0208 604/122 |
| 2014/0074034 A1 | 3/2014 | Tanabe et al. | |
| 2015/0151089 A1 | 6/2015 | Tan | |

FOREIGN PATENT DOCUMENTS

| | | |
|---|---|---|
| JP | H11-4894 A | 1/1999 |
| JP | 2001-046507 A | 2/2001 |
| JP | 2002-263197 A | 9/2002 |
| JP | 2012-517326 A | 8/2012 |
| JP | 2016-013359 A | 1/2016 |
| JP | 5877196 B2 | 3/2016 |
| WO | 2009/137396 A1 | 11/2009 |
| WO | 2013/188103 A1 | 12/2013 |
| WO | 2015/141366 A1 | 9/2015 |

OTHER PUBLICATIONS

Oct. 30, 2018 Search Report issued in International Patent Application No. PCT/JP2018/029139.
Feb. 4, 2020 International Preliminary Report on Patentability issued in International Patent Application No. PCT/JP2018/029139.
May 25, 2021 Invitation pursuant to Rule 62a(1) EPC issued in European Patent Application No. 18 841 085.6.
Jul. 5, 2021 Office Action issued in Chinese Patent Application No. 201880050192.3.
Aug. 26, 2021 extended European Search Report issued in European Patent Application No. 18 841 085.6.
Feb. 22, 2022 Office Action issued in Chinese Patent Application No. 201880050192.3.
May 20, 2022 Office Action issued in Japanese Patent Application No. 2019-534593.
May 30, 2022 Office Action issued in Chinese Patent Application No. 201880050192.3.
Dec. 5, 2022 Office Action issued in Chinese Patent Application No. 201880050192.3.
May 30, 2023 Office Action issued in European Patent Application No. 18841085.6.
Dec. 10, 2024 Office Action issued in Canadian Patent Application No. 3,071,818.

* cited by examiner

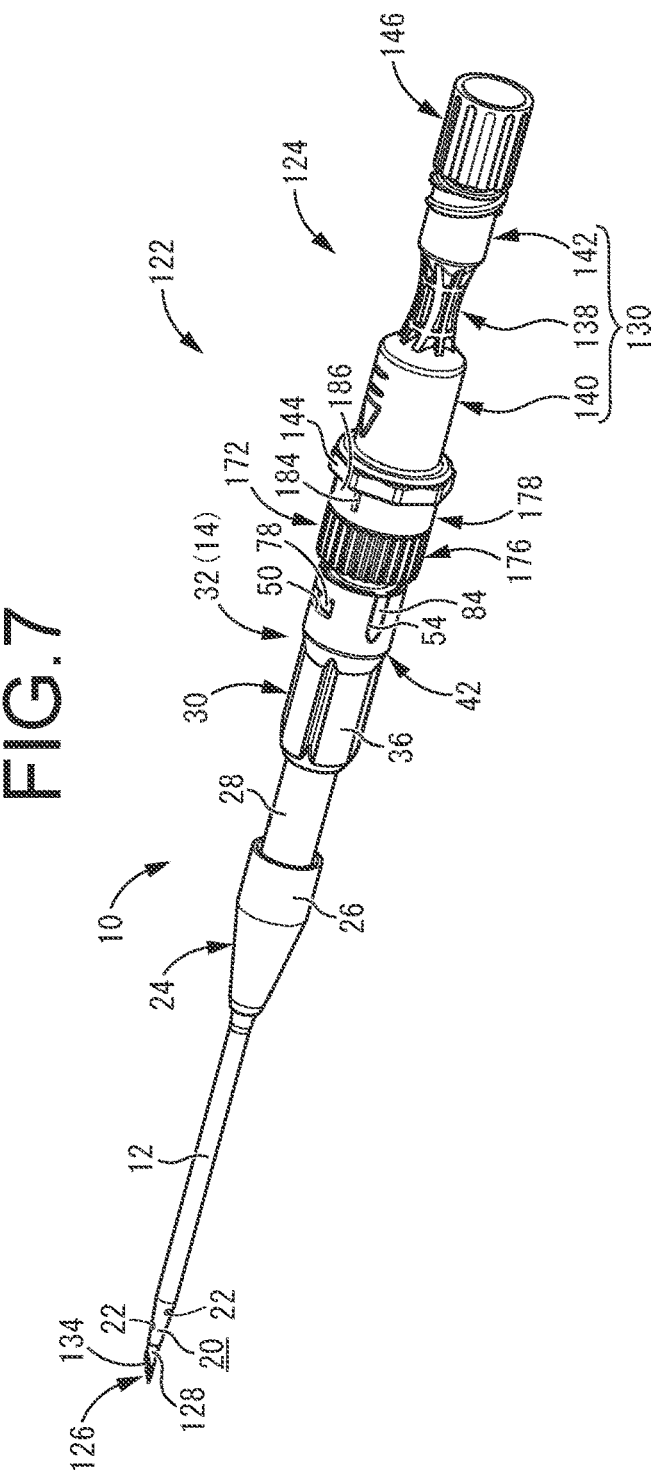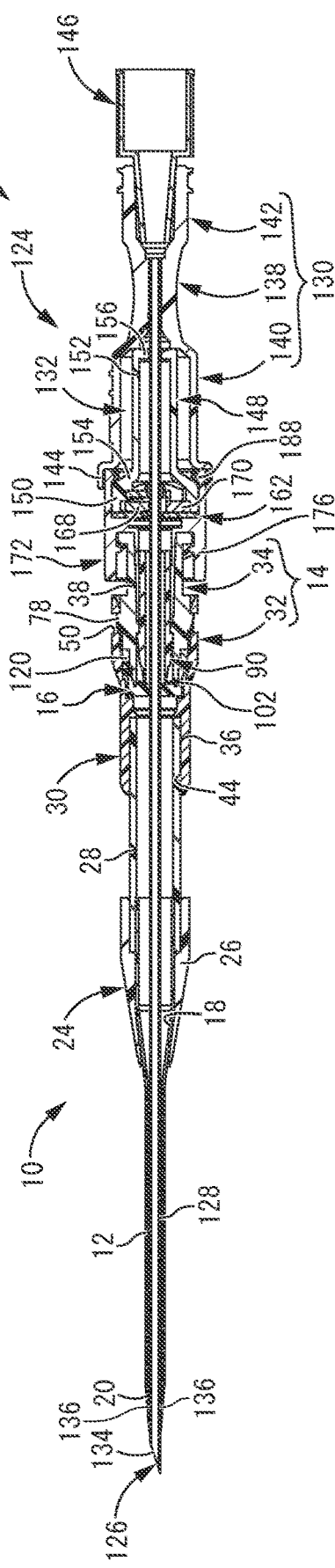

HEMOSTASIS VALVE-EQUIPPED INDWELLING NEEDLE AND INDWELLING NEEDLE ASSEMBLY

This is a Divisional Application of U.S. patent application Ser. No. 16/635,219 filed Jan. 30, 2020, which is a national phase of PCT/JP2018/029139, filed Aug. 2, 2018, which in turn claims the benefit of Japanese Patent Application No. 2017-150204, filed Aug. 2, 2017 and Japanese Patent Application No. 2017-216744, filed Nov. 9, 2017. The disclosure of the prior applications is hereby incorporated by reference herein in its entirety.

TECHNICAL FIELD

The present invention relates to an indwelling needle and an indwelling needle assembly that are stuck and indwelled in a blood vessel when performing infusion, blood collection, hemodialysis, etc. More particularly, the present invention pertains to a hemostasis valve-equipped indwelling needle and an indwelling needle assembly with a hemostasis valve disposed in an internal flow path.

BACKGROUND ART

Conventionally, during long-term blood collection and infusions (including blood transfusions) such as dialysis, and multiple blood collections and infusions for hospitalized patients, used are an indwelling needle or an indwelling needle assembly with a cannula that is maintained in the state of percutaneous puncture into blood vessels.
As such an indwelling needle or an indwelling needle assembly, known example is the one as described in Japanese Patent No. JP-B-5877196 (Patent Document 1) or the like, which includes a cannula (catheter 2) that is percutaneously inserted into a blood vessel and provided on the distal end side, a link connector (catheter hub 3) that can be connected to an external flow path and is provided on the proximal end side, and a hemostasis valve (valve element 7) arranged inside the link connector.

Meanwhile, when connecting the external flow path to the link connector, it is desirable to avoid air from entering the body, and it is preferable to discharge the air in the internal flow path extending from the cannula to the link connector. Therefore, in the indwelling needle (indwelling needle assembly) described in Patent Document 1, an air vent passage (communication portion 9) is formed between the inner circumferential surface of the link connector and the outer circumferential surface of the hemostasis valve, and the opening of the passage is closed with a filter (seal member 10) disposed in the cannula. This filter allows gas to pass through but does not allow liquid to pass through, with the aim of discharging air in the internal flow path while preventing blood leakage.

BACKGROUND ART DOCUMENT

Patent Document

Patent Document 1: JP-B-5877196

SUMMARY OF THE INVENTION

Problem the Invention Attempts to Solve

However, in the indwelling needle (indwelling needle assembly) described in Patent Document 1, the filter having a round tubular shape is merely arranged so as to overlap the inner circumferential surface of the link connector. For this reason, it has been revealed that there is a risk that the filter may be easily deformed due to action of pressure of blood etc., and blood may leak due to the occurrence of minute gap.

The present invention has been developed in view of the above-described matters as the background, and it is an object of the present invention to provide a hemostasis valve-equipped indwelling needle and an indwelling needle assembly with a novel structure capable of discharging air in the internal flow path.

Means for Solving the Problem

A first preferred embodiment of the present invention provides a hemostasis valve-equipped indwelling needle comprising: a cannula provided on a distal end side thereof and configured to be percutaneously inserted into a blood vessel; a link connector provided on a proximal end side thereof; an internal flow path extending from the cannula to the link connector; and a hemostasis valve disposed inside the link connector, the hemostasis valve-equipped indwelling needle being characterized in that: the link connector includes an air vent passage that allows the internal flow path to communicate with an external space further on a cannula side than the hemostasis valve; and a filter that allows gas to pass through but does not allow liquid to pass through is mounted in a compressed state on the air vent passage.

According to the hemostasis valve-equipped indwelling needle structured following this preferred embodiment, the internal flow path extending from the cannula to the link connector communicates with the external space through the air vent passage. Thus, the air in the internal flow path is pushed out by blood return after puncture, so as to be discharged to the external space through the air vent passage. Since the filter that allows gas to pass through but does not allow liquid to pass through is provided on the air vent passage, air discharge will be permitted through the air vent passage, and blood leakage can be prevented.

In particular, the filter is mounted in a compressed state with respect to the link connector. Thus, even if pressure is applied to the filter, deformation of the filter will be avoided or the amount of deformation will be kept to a minimum. This prevents a gap from being generated between the filter and the link connector, thereby more reliably preventing blood leakage.

A second preferred embodiment of the present invention provides a hemostasis valve-equipped indwelling needle comprising: a cannula provided on a distal end side thereof and configured to be percutaneously inserted into a blood vessel; a link connector provided on a proximal end side thereof; an internal flow path extending from the cannula to the link connector; and a hemostasis valve disposed inside the link connector, the hemostasis valve-equipped indwelling needle being characterized in that: the link connector includes an air vent passage that communicates with an external space via an air outlet port opening onto a circumferential wall thereof; the internal flow path communicates with the external space further on a cannula side than the hemostasis valve via the air vent passage; and a filter that allows gas to pass through but does not allow liquid to pass through is clasped by a plurality of rigid members and disposed on the air vent passage.

According to the hemostasis valve-equipped indwelling needle structured following this preferred embodiment, the filter is clasped by the rigid members. Thus, the filter is stably held on the air vent passage, thereby preventing blood leakage with high reliability by the filter.

Furthermore, the opening to the external space of the air vent passage is the air outlet port provided on the circumferential wall of the link connector. Thus, for example, the influence of the internal pressure of the link connector on the discharge of air through the air vent passage is reduced, and the air in the internal flow path can be discharged stably.

A third preferred embodiment of the present invention provides the hemostasis valve-equipped indwelling needle according to the second preferred embodiment, wherein at least one of the rigid members constitutes the link connector.

According to the hemostasis valve-equipped indwelling needle structured following this preferred embodiment, by using the rigid member as a constituent component of the link connector, the number of parts can be reduced, the structure can be simplified, and the like.

A fourth preferred embodiment of the present invention provides the hemostasis valve-equipped indwelling needle according to the second or third preferred embodiment, wherein all of the rigid members have a tubular shape.

According to the hemostasis valve-equipped indwelling needle structured following this preferred embodiment, the filter can be clasped about the entire circumference by the tubular rigid member, and the filter can be held more stably. Therefore, leakage of blood and the like can be prevented more advantageously.

A fifth preferred embodiment of the present invention provides the hemostasis valve-equipped indwelling needle according to any of the second to fourth preferred embodiments, wherein one of the rigid members includes an annular support part, the filter includes an annular fitting part, and the annular fitting part is attached externally about the annular support part of the one of the rigid members.

According to the hemostasis valve-equipped indwelling needle structured following this preferred embodiment, the filter can be handled together with one rigid member by externally attaching the filter to the tubular rigid member at the fitting part. This facilitates the work of assembling the filter between the rigid members.

A sixth preferred embodiment of the present invention provides the hemostasis valve-equipped indwelling needle according to the fifth preferred embodiment, wherein the annular fitting part of the filter is sandwiched and compressed radially between the rigid members.

According to the hemostasis valve-equipped indwelling needle structured following this preferred embodiment, the annular fitting part of the filter is radially compressed. Accordingly, the compressed filter prevents leakage of blood and the like through radially between the rigid members more effectively.

A seventh preferred embodiment of the present invention provides the hemostasis valve-equipped indwelling needle according to any of the second to sixth preferred embodiments, wherein the rigid members are axially adjacent to each other, and the filter is sandwiched and compressed axially between the rigid members.

According to the hemostasis valve-equipped indwelling needle structured following this preferred embodiment, the filter is axially compressed between the rigid members. Thus, the filter provides liquid-tight seal axially between the rigid members, thereby preventing blood or the like passing axially between the rigid members.

An eighth preferred embodiment of the present invention provides the hemostasis valve-equipped indwelling needle according to the seventh preferred embodiment, wherein each of the rigid members that are axially adjacent to each other has a tubular shape, the filter is compressed over an entire circumference axially between the rigid members, and an annular compression rib pressed against the filter over an entire circumference projects from at least one of axially opposed faces of the rigid members.

According to the hemostasis valve-equipped indwelling needle structured following this preferred embodiment, the filter is sandwiched and compressed about the entire circumference axially between the tubular rigid member. Accordingly, the filter prevents passage of liquid between the rigid members even more effectively. Moreover, since the compression rib projects from the rigid member, the filter is more strongly pressed against the rigid member at the portion where the compression rib is formed. This makes it possible to more advantageously realize blood passage restriction effect due to the stable holding of the filter or the like.

A ninth preferred embodiment of the present invention provides the hemostasis valve-equipped indwelling needle according to any of the first to eighth preferred embodiments, wherein the link connector includes a guide connector having a flow path constituting the internal flow path, and a connector cover into which a distal end portion of the guide connector is inserted and fixed, and a gap is provided between the guide connector and the connector cover such that the air vent passage includes the gap.

According to the hemostasis valve-equipped indwelling needle structured following this preferred embodiment, the link connector includes the guide connector and the connector cover, and the air vent passage includes the gap between the guide connector and the connector cover. Thus, by inserting and fixing the distal end part of the guide connector with respect to the connector cover, the air vent passage can be easily formed in the link connector.

A tenth preferred embodiment of the present invention provides the hemostasis valve-equipped indwelling needle according to the ninth preferred embodiment, wherein the filter is mounted in a state of being sandwiched and compressed radially between the guide connector and the connector cover.

According to the hemostasis valve-equipped indwelling needle structured following this preferred embodiment, the filter is mounted in a state of being sandwiched and compressed radially between the guide connector and the connector cover. Thus, the filter can be easily mounted onto the link connector.

An eleventh preferred embodiment of the present invention provides the hemostasis valve-equipped indwelling needle according to the ninth or tenth preferred embodiment, wherein the guide connector includes an engaging projection projecting radially outward from an outer circumferential surface thereof, the connector cover includes an engaging hole radially penetrating a circumferential wall thereof, the engaging projection is engaged in the engaging hole by the distal end portion of the guide connector being inserted into the connector cover such that the guide connector and the connector cover are fixed to each other, and the engaging hole communicates with the gap between the guide connector and the connector cover.

According to the hemostasis valve-equipped indwelling needle structured following this preferred embodiment, the engaging projection provided on the outer circumferential surface of the guide connector engages with the engaging hole that penetrates the circumferential wall of the connector cover, so that the guide connector and the connector cover are fixed to each other. Thus, the circumferential relative movement (relative rotation) and the axial relative movement between the guide connector and the connector cover after their assembly can be prevented. In particular, since the engaging hole provided in the circumferential wall of the connector cover communicates with the gap between the guide connector and the connector cover, namely, the air vent passage, the air in the internal flow path is discharged through the engaging hole to the external space. That is, the engaging hole used for engagement with the guide connector can also be skillfully used as the air vent hole (passage), thereby achieving a simple structure and improvement in production efficiency.

A twelfth preferred embodiment of the present invention provides the hemostasis valve-equipped indwelling needle according to any of the ninth to eleventh preferred embodiments, wherein the connector cover includes a concave groove on an inner circumferential surface thereof, an opening part of the concave groove is covered by the hemostasis valve such that a tunnel-like passage surrounded by the hemostasis valve and the connector cover, and the air vent passage includes the tunnel-like passage.

According to the hemostasis valve-equipped indwelling needle structured following this preferred embodiment, the opening of the concave groove provided in the inner circumferential surface of the connector cover is covered with the hemostasis valve, so that the tunnel-like passage surrounded by the hemostasis valve and the connector cover is formed and the air vent passage includes the tunnel-like passage. Thus, the air vent passage can be easily formed with respect to the link connector. In particular, by providing the hemostasis valve between the guide connector and the connector cover, by placing the hemostasis valve at the distal end of the guide connector and superposing the connector cover thereon from the further distal end side, for example, the link connector and the hemostasis valve can be assembled. Thus, the assembly of the hemostasis valve to the link connector and the formation of the air vent passage in the link connector can be achieved simultaneously and easily.

A thirteenth preferred embodiment of the present invention provides the hemostasis valve-equipped indwelling needle according to any of the eighth to twelfth preferred embodiments, wherein the filter is constituted by a material that allows gas to pass through but absorbs liquid.

According to the hemostasis valve-equipped indwelling needle constructed following this preferred embodiment, due to the filter absorbing blood, the passage of the blood through the filter is prevented. By actively holding the blood in the filter, blood leakage through the air vent passage can be prevented.

A fourteenth preferred embodiment of the present invention provides an indwelling needle assembly comprising: the hemostasis valve-equipped indwelling needle according to any of the first to thirteenth preferred embodiments; and a removable inner needle inserted from a proximal end side of the internal flow path toward a distal end side thereof.

According to this preferred embodiment, the indwelling needle assembly that exhibits the effects described in any of the first to thirteenth preferred embodiments can be manufactured.

Meanwhile, there is a hemostasis valve-equipped indwelling needle including an elastic valve body and an axially movable pusher on the fluid flow path of an indwelling needle, wherein the elastic valve body is opened and closed by movement of the pusher toward the distal end side and the proximal end side, thereby enabling the fluid flow path to communicate and close. The present applicant has proposed such a hemostasis valve-equipped indwelling needle in, for example, Japanese Unexamined Patent Publication No. JP-A-2016-013359 (Patent Document 2).

That is, in Patent Document 2, by pushing the external flow path from the proximal end side of the pusher and moving the pusher to the distal end side, the pusher is inserted into the elastic valve body and the elastic valve body is configured to be pushed open. By so doing, the fluid flow path is placed in communication to perform infusion or blood collection. On the other hand, when the infusion or blood collection is completed or interrupted, the external flow path is removed, so that the pusher is moved to the proximal end side due to elastic recovering deformation of the elastic valve body, and the elastic valve body is closed off as well as the fluid flow path is blocked. This prevents leakage of blood or the like when the external channel is removed.

Here, in order to stably block the fluid flow path, it has been required that the pusher is more reliably moved to the proximal end side due to the elastic recovering action of the elastic valve body, and the elastic valve body is stably closed off.

In view of the above-described matters as the background, a fifteenth preferred embodiment of the present invention provides a hemostasis valve-equipped indwelling needle in which a pusher is configured to move to a distal end side and be inserted into an elastic valve body such that the elastic valve body is pushed open, and the pusher inserted into the elastic valve body is configured to be moved to a proximal end side due to a recovering action of the elastic valve body such that the elastic valve body is closed off, the hemostasis valve-equipped indwelling needle being characterized in that an insertion region of the pusher into the elastic valve body includes a steep-inclined surface on an outer circumferential surface in an axially middle portion thereof, the steep-inclined surface having an inclination angle greater than that on a distal end side thereof.

According to the hemostasis valve-equipped indwelling needle structured following this preferred embodiment, the steep-inclined surface having a larger inclination angle than that of the distal end side is provided in the insertion region of the pusher into the elastic valve body. Thus, when the external flow path is connected (when the pusher moves toward the distal end side), the elastic valve body and the steep-inclined surface come into contact with each other, so that, for example, in comparison with the hemostasis valve-equipped indwelling needle described in Patent Document 1 (a hub assembly with a partition wall member), where the insertion region of the pusher is a tapered surface having a single inclination angle, the axial component in the recovery force of the elastic valve body exerted on the steep-inclined surface when the external flow path is removed can be made larger. As a result, the force for moving the pusher toward the proximal end side can be stably applied, and the movement of the pusher toward the proximal end side, namely, the closing off of the elastic valve body, and the blocking of the fluid flow path can be more reliably achieved. Further, when the pusher is moved to the distal end side, the movement resistance is small, while when the pusher is returned to the proximal end side, a large force for moving the pusher to the proximal end side can be obtained.

A sixteenth preferred embodiment of the present invention provides the hemostasis valve-equipped indwelling needle according to the fifteenth preferred embodiment, wherein a distal end inclined surface having a tapered shape is provided on a distal end side of the steep-inclined surface.

According to the hemostasis valve-equipped indwelling needle structured following this preferred embodiment, even if, for example, the amount of pushing of the external flow path, namely, the amount of movement of the pusher to the distal end side is small, and the amount of contact between the steep-inclined surface and the elastic valve body is small when the external flow path is connected (when the pusher moves to the distal end side), by the distal end inclined surface having a tapered shape and the elastic valve body coming into contact with each other, at the time of removal of the external flow path, the recovery force of the elastic valve body is effectively exerted on the distal end inclined surface, whereby the pusher can be moved to the proximal end side more stably.

A seventeenth preferred embodiment of the present invention provides the hemostasis valve-equipped indwelling needle according to the fifteenth or sixteenth preferred embodiment, wherein a proximal end inclined surface having a tapered shape is provided on a proximal end side of the steep-inclined surface.

According to the hemostasis valve-equipped indwelling needle structured following this preferred embodiment, even if, for example, the amount of pushing of the external flow path, namely, the amount of movement of the pusher to the distal end side is large, it is possible to utilize the recovery force of the elastic valve body exerted on the proximal end inclined surface, whereby the pusher can be moved to the proximal end side more reliably.

An eighteenth preferred embodiment of the present invention provides the hemostasis valve-equipped indwelling needle according to any of the fifteenth to seventeenth preferred embodiments, wherein the steep-inclined surface has a tapered shape.

According to the hemostasis valve-equipped indwelling needle structured following this preferred embodiment, the change in angle with respect to the axial direction in the insertion region of the pusher is smaller than in a case where, for example, the steep-inclined surface extends in the axis-perpendicular direction. Thus, the elastic deformation of the valve body can be realized more smoothly, and the insertion resistance to the elastic valve body can be reduced. Further, when the pusher moves to the distal end side and the elastic valve body is elastically deformed, the possibility that a gap is generated between the steep-inclined surface of the pusher and the elastic valve body is reduced, so that a large contact area of the steep-inclined surface and the valve body can be obtained. This makes it possible to more reliably exert the recovery force of the elastic valve body on the steep-inclined surface.

A nineteenth preferred embodiment of the present invention provides the hemostasis valve-equipped indwelling needle according to any of the fifteenth to eighteenth preferred embodiments, wherein the inclination angle of the steep-inclined surface is constant.

According to the hemostasis valve-equipped indwelling needle structured following this preferred embodiment, the gap between the steep-inclined surface of the pusher and the elastic valve body, which is generated when the pusher moves to the distal end side and the elastic valve body is elastically deformed, can be made small. Thus, it is also possible to obtain a large contact area of the steep-inclined surface and the elastic valve body, thereby more reliably exerting the recovery force of the elastic valve body on the steep-inclined surface.

A twentieth preferred embodiment of the present invention provides the hemostasis valve-equipped indwelling needle according to any of the fifteenth to nineteenth preferred embodiments, wherein a distal end inclined surface and a proximal end inclined surface each having a tapered shape are provided respectively on a distal end side and on a proximal end side of the steep-inclined surface, and the distal end inclined surface has an inclination angle greater than that of the proximal end inclined surface.

According to the hemostasis valve-equipped indwelling needle structured following the present preferred embodiment, by providing the distal end inclined surface and the proximal end inclined surface that are tapered, the effects of the sixteenth and seventeenth preferred embodiments can be compatibly achieved. Specifically, the pusher can be stably moved to the proximal end side when the external flow path is removed regardless of whether the amount of pushing of the external flow path (the amount of movement of the pusher toward the distal end side) is large or small. In particular, by setting the inclination angle of the distal end inclined surface larger than the inclination angle of the proximal end inclined surface, the recovery force of the elastic valve body is stably exerted on the distal end inclined surface, and the axial dimension of the proximal end inclined surface and hence the insertion region can be sufficiently obtained.

A twenty-first preferred embodiment of the present invention provides the hemostasis valve-equipped indwelling needle according to any of the fifteenth to twentieth preferred embodiments, wherein a distal end inclined surface and a proximal end inclined surface each having a tapered shape are provided respectively on a distal end side and on a proximal end side of the steep-inclined surface, and inclination angles of the steep-inclined surface, the distal end inclined surface, and the proximal end inclined surface are all constant.

According to the hemostasis valve-equipped indwelling needle structured following this preferred embodiment, the insertion region can be formed in a generally tapered shape overall, and the insertion resistance to the elastic valve body can be reduced as well. In addition, when the elastic valve body is elastically deformed, it is possible to bring the roughly entire insertion region and the elastic valve body into contact with each other without a substantial gap, and the recovery force of the elastic valve body can be exerted on the pusher more stably.

A twenty-second preferred embodiment of the present invention provides the hemostasis valve-equipped indwelling needle according to any of the fifteenth to twenty-first preferred embodiments, wherein a tubular housing that houses the elastic valve body and the pusher is provided, the pusher includes a contact part on an outer circumferential surface thereof further on a proximal end side than the insertion region, the tubular housing includes a locking protrusion on an inner circumferential surface thereof, and movement of the pusher to the proximal end side is restricted by contact of the contact part and the locking protrusion.

According to the hemostasis valve-equipped indwelling needle structured following this preferred embodiment, a movement restricting mechanism of the pusher toward the proximal end when the external flow path is removed is provided. Specifically, by adopting the fifteenth preferred embodiment, the pusher is likely to move to the proximal end side when the external flow path is removed. However, by providing the movement restricting mechanism as in this preferred embodiment, it is possible to effectively prevent the pusher from dropping out of the housing when the external flow path is removed.

A twenty-third preferred embodiment of the present invention provides the hemostasis valve-equipped indwelling needle according to any of the fifteenth to twenty-second preferred embodiments, wherein a tubular housing that houses the elastic valve body and the pusher is provided, the tubular housing includes an outside housing and an inside housing that are attached to each other by the inside housing being inserted into the outside housing, the elastic valve body includes a tubular support part projecting to the proximal end side on an outer circumferential portion thereof, and the elastic valve body is supported by the tubular housing in a compressed state where the tubular support part is radially clasped by the outside housing and the inside housing.

According to the hemostasis valve-equipped indwelling needle structured following this preferred embodiment, the housing has a divided structure including the outside housing and an inside housing, and the elastic valve body is clasped and supported between the outside housing and the inside housing. By so doing, the assembly of the elastic valve body to the housing can be facilitated. In particular, the elastic valve body is provided with the tubular support part projecting to the proximal end side, and the tubular support part is supported in a compressed state radially between the outside housing and the inside housing. Accordingly, when the external flow path is connected, namely, when the pusher is inserted into the elastic valve body from the proximal end side, the elastic valve body can be effectively prevented from dropping out of the housing.

A twenty-fourth preferred embodiment of the present invention provides the hemostasis valve-equipped indwelling needle according to any of the fifteenth to twenty-third preferred embodiments, wherein the inclination angle of the steep-inclined surface is set within a range of 25 to 75 degrees.

According to the hemostasis valve-equipped indwelling needle structured following this preferred embodiment, by setting the inclination angle of the steep-inclined surface within the above range, the elastic recovery force of the elastic valve body can be efficiently applied to the pusher as a moving force to the proximal end side.

A twenty-fifth preferred embodiment of the present invention provides the hemostasis valve-equipped indwelling needle according to any of the fifteenth to twenty-fourth preferred embodiments, wherein the pusher includes a tapered outer circumferential surface having a tapered shape on an outer circumferential surface in a distal end portion thereof, the tapered outer circumferential surface including the steep-inclined surface, and an axial dimension of a formation part of the tapered outer circumferential surface in the pusher is not less than 4 mm.

According to the hemostasis valve-equipped indwelling needle structured following the present preferred embodiment, for example, the tapered outer circumferential surface having a dimension equal to or larger than the above-mentioned dimension is provided at the distal end portion of the pusher. By so doing, it is also possible, for example, to form the distal end inclined surface according to the sixteenth preferred embodiment and/or the proximal end inclined surface according to the seventeenth preferred embodiment with sufficient axial dimensions, thereby achieving the effects described in the sixteenth and/or seventeenth preferred embodiments more stably.

Effect of the Invention

According to the hemostasis valve-equipped indwelling needle and the indwelling needle assembly structured fol-lowing the present invention, a stable air venting effect is exhibited by mounting the filter in a compressed state on the air vent passage.

BRIEF DESCRIPTION OF THE DRAWINGS

FIG. 7 is a perspective view showing a specific example of an indwelling needle assembly including the hemostasis valve-equipped indwelling needle shown in FIG. 1.

FIG. 8 is a vertical cross sectional view of the indwelling needle assembly shown in FIG. 7.

EMBODIMENTS FOR CARRYING OUT THE INVENTION

Figure 1:
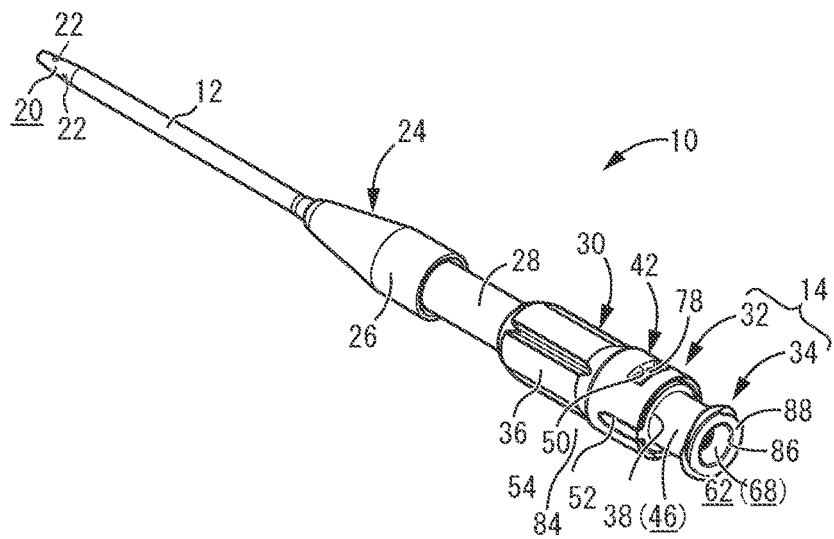
FIG. 1 is a perspective view of a hemostasis valve-equipped indwelling needle according to a first practical embodiment of the present invention.

In order to clarify the present invention more specifically, practical embodiments of the present invention will be described in detail below in reference to the drawings.

First, FIGS. 1 to 6 show a hemostasis valve-equipped indwelling needle 10 as a first practical embodiment of the present invention. This hemostasis valve-equipped indwelling needle 10 includes a cannula 12 serving as a hollow needle on the distal end side thereof, and a link connector 14 serving as a housing to which an external flow path is connected on the proximal end side of the cannula 12. A disc valve 16 serving as a hemostasis valve (elastic valve body) is accommodated in the link connector 14. An internal flow path 18 is constituted by including the insides of the cannula 12 and the link connector 14. By the cannula 12 being percutaneously inserted into a patient's blood vessel and indwelled therein, infusion or blood collection is performed through the internal flow path 18. Also, due to the external flow path being connected to and removed from the link connector 14, opening and closing of the disc valve 16, that is, communication and blocking of the internal flow path 18 are switched. In the following description, the axial direction refers to the left-right direction in FIG. 2, which is the central axis direction of each member, and roughly corresponds to the needle axis direction of the cannula 12 that is a hollow needle, and which is the length direction. Further, the distal end side refers to the left side in FIG. 2 which is the side where the cannula 12 is stuck, while the proximal end side refers to the right side in FIG. 2 which is the side operated by the user.

More specifically, the cannula 12 is formed of a soft synthetic resin in the present practical embodiment, and the outer circumferential surface of the distal end portion constitutes a tapered outer circumferential surface 20 whose outer diameter dimension gradually decreases toward the distal end side. A plurality of passage holes 22 are formed in the circumferential wall of the tip portion of the cannula 12 so that blood or the like can easily flow into the cannula 12 through the passage hole 22. In addition, the material of the cannula 12 is not limited to a soft synthetic resin, but may be a metal, for example.

The proximal end portion of the cannula 12 is fixedly supported by a needle hub 24. The needle hub 24 includes a roughly tubular circumferential wall 26, and is formed of, for example, a rigid synthetic resin. Then, the cannula 12 is inserted into the needle hub 24 and the proximal end portion of the cannula 12 is fixed to the needle hub 24 by adhesion or welding, so that the cannula 12 extends from the needle hub 24 to the distal end side.

An elastic tube 28 is connected to the proximal end side of the needle hub 24. The elastic tube 28 is formed of, for example, soft synthetic resin, and the distal end portion of the elastic tube 28 is sandwiched between the circumferential wall 26 of the needle hub 24 and the cannula 12 at the proximal end opening part of the needle hub 24, and subjected to bonding or welding as necessary. Accordingly, the elastic tube 28 is connected to the proximal end side of the needle hub 24. By so doing, the cannula 12 and the elastic tube 28 are firmly fixed to the needle hub 24.

The proximal end portion of the elastic tube 28 is fixed to the distal end portion of the link connector 14. The link connector 14 has a generally tubular shape overall. The proximal end portion of the elastic tube 28 is inserted from the distal end opening part of the link connector 14 and is subjected to bonding or welding as necessary. By so doing, the elastic tube 28 and the link connector 14 are connected. That is, the distal end portion of the link connector 14 constitutes a tube connecting part 30 to which the elastic tube 28 is connected.

The internal flow path 18 extending from the cannula 12 to the link connector 14 is constituted by the inner holes of the cannula 12, the elastic tube 28, and the link connector 14 (particularly, a pusher 90 described later provided inside the link connector 14).

The link connector 14 of the present practical embodiment has a shape in which a connector cover 32 serving as an outside housing and a guide connector 34 serving as an inside housing both having a generally round tubular shape are coupled and fixed to each other in the axial direction. That is, the connector cover 32 is fixed to the distal end portion of the guide connector 34 by inserting and assembling the distal end side of the guide connector 34 to the proximal end side of the connector cover 32, and the link connector 14 is constituted. The circumferential wall of the link connector 14 is constituted by a circumferential wall 36 of the connector cover 32 and a circumferential wall 38 of the guide connector 34. In addition, the distal end portion of the circumferential wall 38 of the guide connector 34 that is inserted into the connector cover 32 comprises an insertion part 40 having a generally round tubular shape. On the other hand, the proximal end portion of the circumferential wall 36 of the connector cover 32, into which the insertion part 40 of the guide connector 34 is inserted, comprises an insertion target part 42 having a generally round tubular shape.

The proximal end of the guide connector 34 extends further to the proximal end side with a predetermined axial dimension than the connector cover 32. Therefore, the circumferential wall of the link connector 14 has a double wall structure at the portion where the insertion part 40 is inserted into the insertion target part 42, which is the coupling portion of the connector cover 32 and the guide connector 34. Meanwhile, the circumferential wall on the distal end side of the link connector 14 is constituted by the circumferential wall 36 of the connector cover 32, and the circumferential wall on the proximal end side of the link connector 14 is constituted by the circumferential wall 38 of the guide connector 34. That is, a proximal end portion 44a on an inner circumferential surface 44 of the connector cover 32 (inner circumferential surface of the insertion target part 42) and a distal end portion 46a of an outer circumferential surface 46 of the guide connector 34 (outer circumferential surface of the insertion part 40) are overlapped on each other, so that the connector cover 32 and the guide connector 34 are coupled to form a double wall structure.

The connector cover 32 is made of a rigid synthetic resin and includes the roughly tubular circumferential wall 36. On the inner circumferential surface 44 in the axially middle portion of the circumferential wall 36, an annular wall part 48 is formed so as to protrude toward the radially inner side. The proximal end of the elastic tube 28 inserted from the distal end opening part of the connector cover 32 is in contact with the distal end surface of the annular wall part 48. Thus, the portion of the connector cover 32 further on the distal end side than the annular wall part 48 constitutes the tube connecting part 30 to which the elastic tube 28 is connected.

In the connector cover 32, the inner diameter dimension and the outer diameter dimension of the tube connecting part 30 which is the distal end side are roughly constant over roughly the entire length in the axial direction. In addition, the inner diameter dimension and the outer diameter dimension of the insertion target part 42 which is the proximal end side are larger than those of the tube connecting part 30, and are roughly constant over roughly the entire length in the axial direction.

Figure 2:
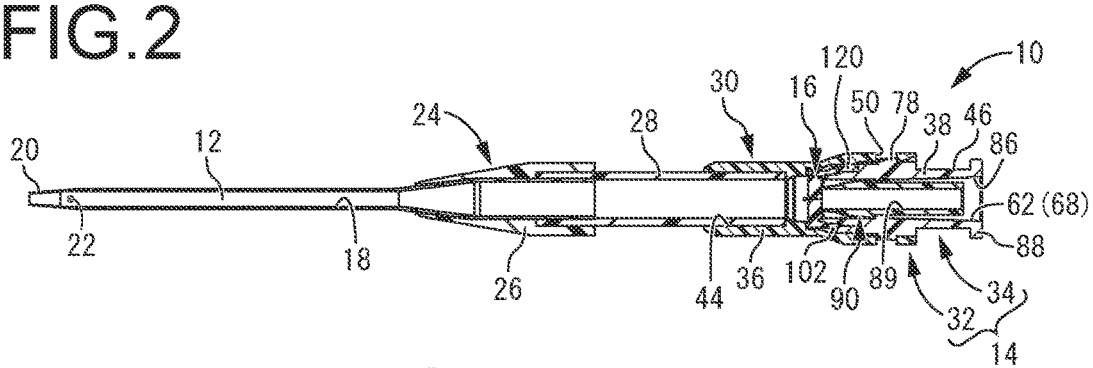
FIG. 2 is a vertical cross sectional view of the hemostasis valve-equipped indwelling needle shown in FIG. 1.
Figure 3:
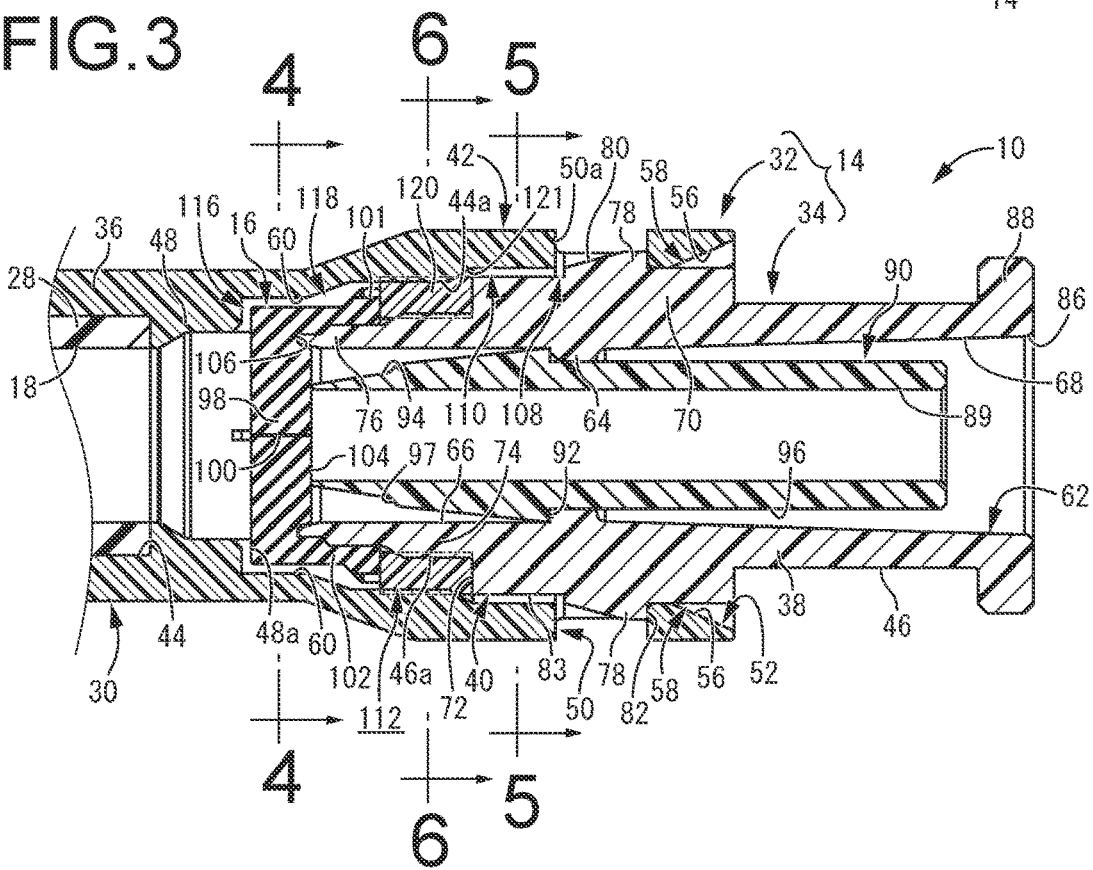
FIG. 3 is an enlarged vertical cross sectional view of a principal part in FIG. 2.

Further, in the insertion target part 42 in the circumferential wall 36 of the connector cover 32, a pair of engaging holes 50, 50 penetrating the circumferential wall 36 in the thickness direction (radial direction) on opposite sides in one diametrical direction (opposite sides in the vertical direction in FIG. 2). Each of the engaging holes 50, 50 has a generally rectangular shape in a plan view, and is formed with a circumferential dimension that is less than ½ the circumference. Besides, in the circumferential wall 36 of the connector cover 32, at the location away from the pair of engaging holes 50, 50 in the circumferential direction, there are formed notches 54 extending from the opening edge of the proximal end opening part 52 toward the axially inner side (distal end side). In the present practical embodiment, a pair of notches 54, 54 are formed with a predetermined width dimension on opposite sides in the direction orthogonal to the direction of opposition of the pair of engaging holes 50, 50 (opposite sides in the front-rear direction of the paper surface in FIG. 2).

Furthermore, on the inner circumferential surface 44 of the insertion target part 42 of the connector cover 32, a pair of inclined surfaces 56, 56 are formed in the proximal end opening part 52. These inclined surfaces 56, 56 are formed in the same direction as the direction of opposition of the engaging holes 50, 50 (opposite sides in the vertical direction in FIG. 2), and the thickness dimension of the circumferential wall 36 gradually decreases toward the proximal end side. A pair of inclined grooves 58, 58 opened to the radially inner side are formed in the proximal end opening part 52 of the connector cover 32 by the inclined surfaces 56, 56 and the wall portions on both sides in the circumferential direction of the inclined surfaces 56, 56. In addition, the widthwise dimension of the inclined surfaces 56, 56 is roughly equal to the widthwise dimension of the engaging holes 50, 50, and the engaging holes 50, 50 and the inclined grooves 58, 58 are partially formed on the circumference at corresponding positions to each other in the circumferential wall 36 of the connector cover 32. That is, the engaging holes 50, 50 are formed on the distal end side of the inclined grooves 58, 58.

Figure 4:
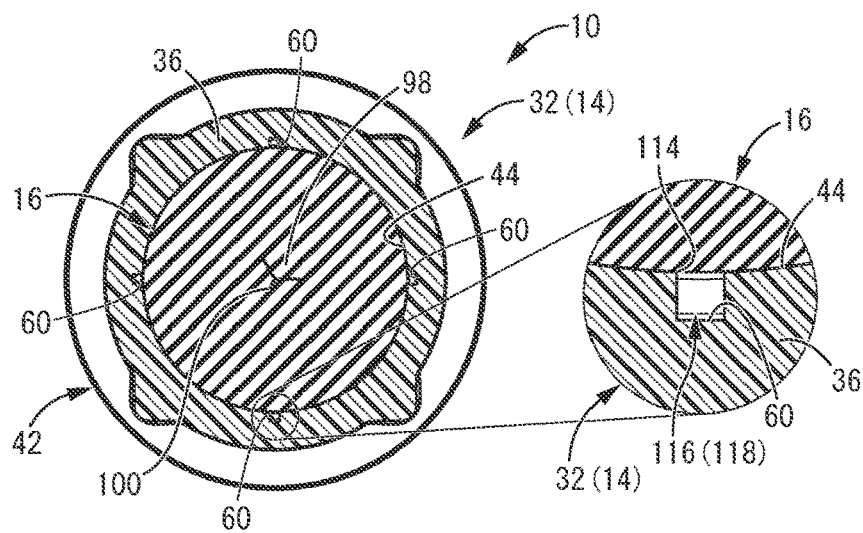
FIG. 4 is a cross sectional view taken along line 4-4 of FIG. 3.

As shown in FIG. 4, on the inner circumferential surface 44 of the connector cover 32, there are formed concave grooves 60 extending in the radial direction on the proximal end surface 48a of the annular wall part 48 and further extending from the proximal end surface 48a to the proximal end side. The concave groove 60 has a generally rectangular cross section, and opens to the proximal end side on the proximal end surface 48a of the annular wall part 48, while opening to the radially inner side on the inner circumferential surface 44 of the circumferential wall 36. In the present practical embodiment, four concave grooves 60, 60, 60, 60 are formed at roughly equal intervals on the circumference. One pair of concave grooves 60, 60 are formed at positions corresponding to the engaging holes 50, 50 on the circumference, while the other pair of concave grooves 60, 60 are formed at positions corresponding to the notches 54, 54 on the circumference. These concave grooves 60, 60, 60, 60 are each formed with a predetermined axial dimension.

On the other hand, the guide connector 34 is formed of a rigid synthetic resin and includes the circumferential wall 38 having a smaller diameter than that of the circumferential wall 36 of the connector cover 32. The circumferential wall 38 has an inner diameter dimension that is roughly constant over roughly the entire length in the axial direction, while having an outer diameter dimension that changes in the axial direction.

That is, on an inner circumferential surface 62 of the guide connector 34 (circumferential wall 38), an annular locking wall part 64 serving as a locking protrusion is formed in the axially middle portion so as to protrude toward the radially inner side. In the inner circumferential surface 62 of the guide connector 34, the distal end side of the locking wall part 64 comprises a guide surface 66 that guides the axial movement of a pusher 90 described later, and the inner diameter dimension thereof is roughly constant. On the other hand, the proximal end side of the locking wall part 64 comprises a tapered surface 68 whose inner diameter dimension gradually increases toward the proximal end side.

Further, the distal end portion 46a of the outer circumferential surface 46 of the guide connector 34, that is, the outer circumferential surface 46a of the insertion part 40 is reduced in diameter in a stepwise manner toward the distal end side. That is, a contact part 70 whose outer diameter dimension is roughly constant is provided on the proximal end side of the insertion part 40, and the outer diameter dimension of the contact part 70 is roughly equal to the inner diameter dimension of the insertion target part 42.

Further, on the outer circumferential surface 46a of the insertion part 40, an annular step surface 72 that extends in the radial direction is formed at the axially middle portion. That is, the proximal end side of the step surface 72 comprises the contact part 70, while the distal end side of the step surface 72 comprises an annular support part 74 having a smaller outer diameter dimension than that of the contact part 70. The annular support part 74 has a predetermined axial dimension, and an insertion tube part 76 having an even smaller outer diameter dimension is formed further on the distal end side.

Furthermore, engaging projections 78 that project to the radially outer side are provided on the outer circumferential surface of the contact part 70 in the outer circumferential surface 46a of the insertion part 40. In the present practical embodiment, a pair of engaging projections 78, 78 are formed on opposite sides in one diametrical direction (opposite sides in the vertical direction in FIG. 2). The shape of the engaging projections 78, 78 in a plan view is a generally rectangular shape roughly corresponding to the engaging holes 50, 50 in the connector cover 32. And the distal side end faces of the engaging projections 78, 78 comprise inclined surfaces 80, 80 where the projecting height of the engaging projections 78, 78 gradually decreases toward the distal end side, while the proximal side end faces comprise vertical surface 82, 82 extending in the roughly axis-perpendicular direction. In addition, the inclination direction of the inclined surfaces 80, 80 of the engaging projections 78, 78 with respect to the axial direction is equal to the inclination direction of the inclined surfaces 56, 56 of the inclined grooves 58, 58 with respect to the axial direction. In the present practical embodiment, the inclination angles of the two inclined surfaces 56, 80 with respect to the axial direction are also roughly equal, and the inclined surface 56 and the inclined surface 80 are roughly parallel to each other in the axial direction. The number of the engaging projections 78 and the engaging holes 50 is not limited to two (a pair), but one or three or more may be provided on the circumference.

Figure 5:
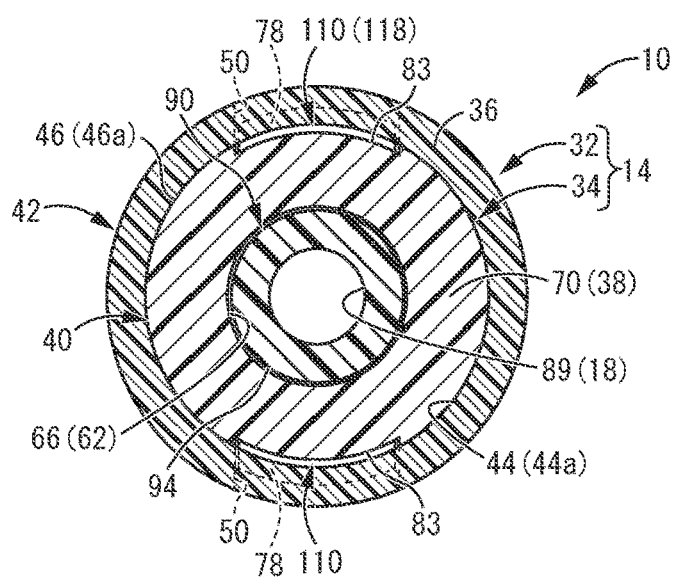
FIG. 5 is a cross sectional view taken along line 5-5 of FIG. 3.

Further, as shown in FIG. 5, in the outer circumferential surface of the contact part 70, concave parts 83, 83 that open to the radially outer side are formed on the distal end side of the engaging projections 78, 78. These concave parts 83, 83 have roughly the same circumferential dimension as that of the engaging projections 78, 78, and are formed on the outer circumferential surface of the contact part 70 over the entire length on the distal end side of the engaging projections 78, 78. That is, these concave parts 83, 83 are open to the distal end side. By providing the concave parts 83, 83, the outer diameter dimension of the contact part 70 is roughly equal to the inner diameter dimension of the insertion target part 42 except for the position where the concave parts 83, 83 are formed, while in the position where the concave parts 83, 83 are formed, the outer diameter dimension of the contact part 70 is made smaller by the depth dimension (radial dimension) of the concave parts 83, 83 than the inner diameter dimension of the insertion target part 42.

Further, on the outer circumferential surface 46a of the insertion part 40, on opposite sides in the direction orthogonal to the direction in which the pair of engaging projections 78, 78 are opposed to each other (opposite sides in the front-rear direction of the paper surface in FIG. 2), there are formed a pair of positioning projections 84, 84 having a shape roughly corresponding to the notches 54, 54 of the connector cover 32 so as to protrude therefrom.

In the guide connector 34, the proximal end side beyond the insertion part 40 extends roughly straight with an outer diameter dimension smaller than that of the insertion part 40, and on a proximal end opening part 86, there is formed a roughly annular flange part 88 protruding to the radially outer side. A male thread is formed on the outer circumferential surface of the flange part 88, so that a luer-lock type external flow path can be connected when an external flow path to be described later is connected.

On the radially inner side of the guide connector 34 having such a shape, a tubular pusher 90 having an inner hole 89 penetrating in the axial direction at the center is accommodated. As will be described later, the internal flow path 18 of the hemostasis valve-equipped indwelling needle 10 is constituted by including the inner hole 89 of the pusher 90. Thus, in other words, the guide connector 34 includes the flow path (inner hole 89 of the pusher 90) constituting the internal flow path 18. The inner diameter dimension of the pusher 90 is roughly constant over roughly the entire length in the axial direction. Meanwhile, on the outer circumferential surface of the pusher 90, an annular step surface (contact part) 92 extending in the axis-perpendicular direction is provided. In the outer circumferential surface of the pusher 90, the distal end side of the step surface 92 comprises a tapered outer circumferential surface 94 that gradually decreases in diameter toward the distal end side, while the proximal end side of the step surface 92 comprises a straight outer circumferential surface 96 having a roughly constant outer diameter dimension. Note that the maximum outer diameter dimension of the proximal end portion of the tapered outer circumferential surface 94 is larger than the outer diameter dimension of the straight outer circumferential surface 96. Further, the tapered outer circumferential surface 94 provided in the insertion region of the pusher 90 into the disc valve 16 includes a taper-shaped steep-inclined surface 97 at the axially middle portion thereof. The inclination angle of the steep-inclined surface 97 with respect to the axial direction is larger than the inclination angle of the distal end side beyond the steep-inclined surface 97 in the tapered outer circumferential surface 94 (distal end inclined surface), and is larger than the inclination angle of the proximal end side beyond the steep-inclined surface 97 in the tapered outer circumferential surface 94 (proximal end inclined surface).

Here, the disc valve 16 is accommodated between the connector cover 32 and the guide connector 34 inside the link connector 14. The disc valve 16 has a roughly disk shape and is formed of a material having elasticity such as rubber, elastomer, and the like. A slit 100 penetrating in the axial direction is formed in the central portion 98 of the disc valve 16. Although the shape of the slit 100 is not limited, in the present practical embodiment, the slit 100 has a radial shape extending roughly uniformly (approximately every 120 degrees) in three directions in the circumferential direction. In addition, in the isolated state of the disc valve 16 before being assembled to the link connector 14, the outer diameter dimension of the disc valve 16 is larger than the inner diameter dimension of the connector cover 32. By the disc valve 16 being assembled to the link connector 14, a radial pressing force is exerted on the disc valve 16 from the radially outer side toward the radially inner side, for example, so that the slit 100 is stably closed off. That is, a pressing part that presses the outer circumferential surface of the disc valve 16 in the radial direction is provided on the inner circumferential surface of the link connector 14. In the present practical embodiment, the outer diameter dimension of the distal end portion of the disc valve 16 in the isolated state is made larger than the inner diameter dimension of the connector cover 32. By the disc valve 16 being assembled to the link connector 14, a radial pressing force is exerted from the radially outer side toward the radially inner side, for example, so that the slit 100 is stably closed off. Here, the outer diameter dimension of the proximal end portion of the disc valve 16 (proximal end portion of a tubular support part 102 described later) is smaller than the inner diameter dimension of the connector cover 32 over the entire circumference or partially on the circumference. Accordingly, a thickness relief part 101 that is an internal space is provided radially between the disc valve 16 and the connector cover 32 at the proximal end portion of the disc valve 16. Therefore, when the disc valve 16 is assembled to the link connector 14, even in the case where the distal end portion of the disc valve 16 is pressed so that a force is applied to deform the proximal end portion of the disc valve 16 so as to expand in the radial direction, since the escape site for the compression force is prepared by the thickness relief part 101, the disc valve 16 can be easily assembled.

A tubular support part 102 extending toward the proximal end side is provided on the outer circumferential portion of the disc valve 16. In addition, in the outer circumferential portion of a proximal end side surface 104 of the disc valve 16, on the radially inner side than the tubular support part 102, there is formed an annular circumferential groove 106 that continuously extends over the entire circumference in the circumferential direction and opens to the proximal end side.

The link connector 14 includes the connector cover 32 and the guide connector 34 having the above-described structure, and the disc valve 16 and the pusher 90 are assembled inside the link connector 14.

Specifically, the pusher 90 is inserted from the distal end opening part of the guide connector 34 and disposed. At that time, the proximal end position of the pusher 90 is determined by the locking wall part 64 provided on the inner circumferential surface 62 of the guide connector 34 and the step surface 92 provided on the outer circumferential surface of the pusher 90 coming into contact with each other. In the accommodated state of the pusher 90, the straight outer circumferential surface 96 of the pusher 90 and the inner circumferential surface of the locking wall part 64 are in contact with or slightly remote from each other, and the outer circumferential surface of the proximal end portion of the tapered outer circumferential surface 94 of the pusher 90 and the guide surface 66 of the guide connector 34 are in contact with or slightly remote from each other. Accordingly, the pusher 90 is movable in the axial direction while being guided by the inner circumferential surface 62 of the guide connector 34.

The tubular support part 102 of the disc valve 16 is superposed on and supported by the distal end portion of the guide connector 34. That is, the distal end portion of the insertion tube part 76 that is the distal end of the guide connector 34 is inserted into the circumferential groove 106 provided on the proximal end side surface 104 of the disc valve 16. In the present practical embodiment, the inner and outer circumferential surfaces of the distal end portion of the insertion tube part 76 are in contact with or slightly remote from the inner and outer circumferential surfaces constituting the inner surface of the circumferential groove 106. A gap may be provided axially between the distal end surface of the insertion tube part 76 and the groove bottom surface of the circumferential groove 106.

The inner circumferential surface of the tubular support part 102 of the disc valve 16 is in contact with the outer circumferential surface of the insertion tube part 76, and the distal end portion of the guide connector 34 is fitted into the proximal end side of the disc valve 16. In the present practical embodiment, when the disc valve 16 is supported, the distal end of the pusher 90 is in contact with the proximal end side surface 104 of the disc valve 16, and the pusher 90 is positioned axially between the disc valve 16 and the locking wall part 64. The distal end of the pusher 90 is not necessarily in contact with the proximal end side surface 104 of the disc valve 16, but the distal end of the pusher 90 and the proximal end side surface 104 of the disc valve 16 may be remote from each other in the axial direction.

The connector cover 32 is assembled from the distal end side of the disc valve 16. That is, the distal end portion of the guide connector 34 is inserted from the proximal end opening part 52 of the connector cover 32 with the disc valve 16 being superposed on and supported by the distal end thereof, and the engaging projections 78, 78 of the guide connector 34 are engaged with the engaging holes 50, 50 of the connector cover 32, so that the connector cover 32 and the guide connector 34 are coupled and fixed in series in the axial direction on roughly the same central axis. In the assembled state of the connector cover 32 and the guide connector 34, gaps 108, 108 are formed axially between the inclined surfaces 80, 80 that are the distal side end faces of the engaging projections 78, 78, and the distal end inner surfaces 50a, 50a that constitute the inner surfaces of the engaging holes 50, 50.

In the present practical embodiment, since the distal side end faces of the engaging projections 78, 78 comprise the inclined surfaces 80, 80, the engaging projections 78, 78 can be easily fitted into the engaging holes 50, 50. Further, since the proximal side end faces of the engaging projections 78, 78 comprise the vertical surfaces 82, 82, dislodgment of the engaging projections 78, 78 from the engaging holes 50, 50, that is, dislodgment of the guide connector 34 from the connector cover 32, is prevented.

In the present practical embodiment, at the proximal end opening part 52 of the connector cover 32, there are formed the inclined grooves 58, 58 constituted by including the inclined surfaces 56, 56. Thus, when the guide connector 34 is inserted into the connector cover 32, by the engaging projections 78, 78 being inserted into the inclined grooves 58, 58, relative rotation in the circumferential direction between the connector cover 32 and the guide connector 34 can be prevented. Further, since the engaging projections 78, 78 are stably guided to the engaging holes 50, 50 by the guiding action of the inclined surfaces 56, 56, the engaging projections 78, 78 can be more reliably engaged with the engaging holes 50, 50.

Furthermore, when the guide connector 34 is inserted into the connector cover 32, the positioning projections 84, 84 of the guide connector 34 are inserted into the notches 54, 54 provided in the proximal end opening part 52 of the connector cover 32. By so doing, the connector cover 32 and the guide connector 34 are easily positioned in the circumferential direction, so that the engaging projections 78, 78 can be even more reliably engaged with the engaging holes 50, 50.

In the assembled state of the connector cover 32 and the guide connector 34, the contact part 70 provided in the insertion part 40 of the guide connector 34 has the outer diameter dimension that is roughly equal to the inner diameter dimension of the insertion target part 42 in the connector cover 32 other than at the positions where the concave parts 83, 83 are formed. Thus, the connector cover 32 and the guide connector 34 come into contact with each other with almost no gap. On the other hand, the outer diameter dimension of the contact part 70 is reduced at the formation position of the concave parts 83, 83. Thus, by the radially outer side opening of the concave parts 83, 83 being covered with the connector cover 32, as shown in FIG. 5, gaps 110, 110 extending in the axial direction are formed radially between the connector cover 32 and the guide connector 34. The gaps 110, 110 communicate with the engaging holes 50, 50 at their proximal ends, and specifically, communicate with gaps 108, 108 between the engaging projections 78, 78 and the engaging holes 50, 50. In short, the gaps 110, 110 formed radially between the connector cover 32 and the guide connector 34 communicate with the external space via the engaging holes 50, 50 (gaps 108, 108).

Figure 6:
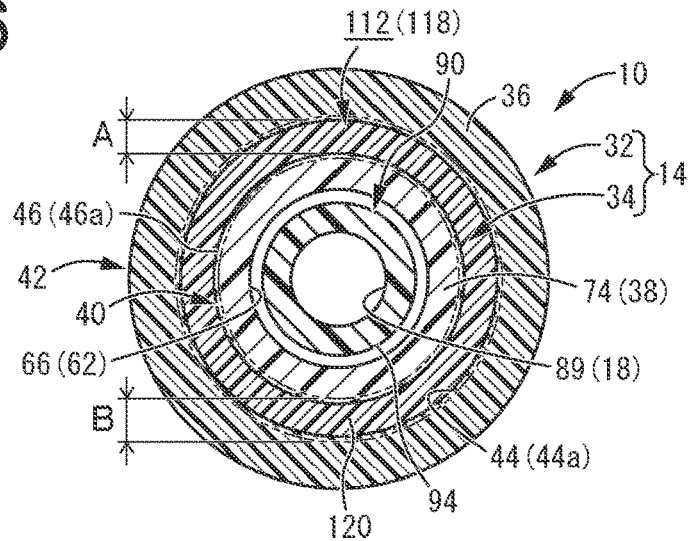
FIG. 6 is a cross sectional view taken along line 6-6 of FIG. 3.

Further, in the guide connector 34, the annular support part 74 having a smaller outer diameter dimension than that of the contact part 70 is formed further on the distal end side than the contact part 70. Accordingly, as shown in FIG. 6, by the connector cover 32 and the guide connector 34 being assembled, a roughly annular accommodation region 112 is provided radially between the circumferential wall 36 of the connector cover 32 and the annular support part 74. The accommodation region 112 communicates with the gaps 110, 110 formed radially between the connector cover 32 and the guide connector 34 located on the proximal end side thereof. In the present practical embodiment, the accommodation region 112 is formed with a predetermined radial width dimension A (see FIG. 6).

In the assembled state of the connector cover 32 and the guide connector 34, the outer circumferential portion of the disc valve 16 is positioned in the axial direction and in the axis-perpendicular direction between the connector cover 32 and the guide connector 34 assembled to each other. By so doing, the disc valve 16 is assembled in a mated state of being mated with the connector cover 32 and the guide connector 34. That is, the outer circumferential portion of the disc valve 16 is clasped axially between the proximal end surface 48a of the annular wall part 48 provided in the connector cover 32 and the insertion tube part 76 that is the distal end portion of the guide connector 34. Further, the tubular support part 102 that protrudes to the proximal end side in the disc valve 16 is clasped radially between the circumferential wall 36 of the connector cover 32 and the insertion tube part 76 preferably in a compressed state. Moreover, the disc valve 16 is assembled so as to be compressed radially inward by the circumferential wall 36 of the connector cover 32. In addition, the proximal end surface of the tubular support part 102 in the disc valve 16 and the distal end surface of a filter 120 described later are in contact with each other in the axial direction with almost no gap.

As described above, the outer surface of the disc valve 16 is overlapped on the inner circumferential surface 44 of the connector cover 32, By so doing, as shown in FIG. 4, opening parts 114, 114, 114, 114 of the concave grooves 60, 60, 60, 60 provided in the inner circumferential surface 44 of the connector cover 32 are covered with the outer surface of the disc valve 16, so as to form tunnel-like passages 116, 116 surrounded by the disc valve 16 and the connector cover 32. That is, the distal end sides of the tunnel-like passages 116, 116, 116, 116 open onto the inner circumferential surface of the annular wall part 48, and communicate with the distal end side (cannula 12 side) beyond the disc valve 16 in the internal flow path 18, while the proximal end sides thereof communicate with the accommodation region 112. It should be noted that the outer circumferential surface of the disc valve 16 is overlapped on the inner circumferential surface 44 of the connector cover 32 in a compressed state, so that the portions of these overlapped faces other than the formation positions of the concave grooves 60, 60, 60, 60 are sealed in a liquid-tight manner.

As a result, in the internal flow path 18, the space on the distal end side with respect to the disc valve 16 communicates with the external space via the tunnel-like passages 116, 116, 116, 116, the accommodation region 112, and the gaps 110, 110 and gaps 108, 108 between the connector cover 32 and the guide connector 34. In other words, an air vent passage 118 that allows the space in the internal flow path 18 further on the distal end side (the cannula 12 side) than the disc valve 16 to communicate with the external space is formed inside the link connector 14 by including the tunnel-like passages 116, 116, 116, 116, the accommodation region 112, and the gaps 110, 110 and the gaps 108, 108 between the connector cover 32 and the guide connector 34. The air vent passage 118 communicates with the external space through the engaging holes 50, 50 opening onto the circumferential wall 36 of the connector cover 32 constituting the link connector 14, and the engaging holes 50, 50 comprise an air outlet port of the present practical embodiment.

Here, as also shown in FIG. 6, a filter 120 is provided in the accommodation region 112 located on the air vent passage 118. The filter 120 has a roughly tubular shape overall. In the present practical embodiment, the outer circumferential portion of the distal end surface of the filter 120 is exposed to the air vent passage 118 (tunnel-like passages 116, 116, 116, 116), while the proximal end portion on the outer circumferential surface of the filter 120 is exposed to the air vent passage 118 (gaps 110, 110). The filter 120 has a property that allows gas to pass through but does not allow liquid to pass through. No limitation is imposed as to the filter 120 as long as it has the above-mentioned properties. For example, a sintered porous material obtained by sintering a polymeric material such as polyethylene and a material containing a hydrophilic, water-soluble or water-swellable polymer, a hydrophobic nonwoven fabric, a porous material, and the like can be suitably adopted. In particular, when a sintered material containing a superabsorbent polymer (SAP) is adopted as the filter 120, gas is allowed to pass through in an initial state until water touches the filter 120, and when water touches the filter 120, the filter 120 reacts with the water (absorbs the water) and swells to prevent its passage, thereby stably exhibiting effects of venting air and preventing blood leakage described later. In addition, the filter 120 of the present practical embodiment comprises an annular (tubular) fitting part overall.

A radial width dimension B of the filter 120 in the isolated state before being assembled to the link connector 14 (shown by the chain double-dashed line in FIG. 6) is larger than the radial width dimension A of the accommodation region 112. That is, by the roughly tubular filter 120 being externally placed on the radially outer side of the annular support part 74 of the guide connector 34, and the distal end portion of the guide connector 34 being inserted into the connector cover 32, the filter 120 is mounted in a state of being sandwiched and compressed in the radial direction by the connector cover 32 and the guide connector 34. In short, the filter 120 is assembled in a state of being pressed against the radially opposing surfaces of the outer circumferential surface of the annular support part 74 and the inner circumferential surface 44 (44a) of the connector cover 32. By so doing, in the present practical embodiment, the rigid members which clasp the filter 120 in the radial direction is defined by the connector cover 32 and the guide connector 34 which constitute the link connector 14. In addition, the filter 120 is assembled so as to be in contact with the axially opposed surfaces of the proximal end surface of the disc valve 16 and the step surface 72 of the guide connector 34 as well, and preferably, the filter 120 is assembled in a compressed state also in the axial direction by these surfaces. In particular, in the present practical embodiment, the axially opposite side surfaces and the radially opposite side surfaces of the filter 120 are pressed against each pressing surface with an area of more than half.

By the connector cover 32, the guide connector 34, the disc valve 16, the pusher 90, and the filter 120 being assembled with the distal end side facing upward, dislodgment of the disc valve 16 from the guide connector 34 or the like during assembly will be effectively prevented, thereby improving assembly efficiency. In the present practical embodiment, in the connector cover 32, the inner diameter of the portion that clasps the filter 120 is smaller than the inner diameter of the opening part on the proximal end side thereof. Accordingly, there is formed an inclined step surface 121 between the clasping portion and the proximal end opening portion, and the inclined step surface 121 has a tapered shape. With this configuration, when the filter 120 attached to the guide connector 34 in an externally fitted state is pushed into the radial inside of the connector cover 32, the filter 120 is guided in contact with the inclined step surface 121, so that the mode of diameter constriction deformation of the filter 120 may be stabilized, thereby disposing the filter 120 in a desired clasped state.

By coupling the cannula 12, the needle hub 24, the elastic tube 28, and the link connector 14 as described above in the axial direction, the hemostasis valve-equipped indwelling needle 10 of the present practical embodiment is constituted. Such a hemostasis valve-equipped indwelling needle 10 is used as an indwelling needle assembly with a hemostasis valve by the hemostasis valve-equipped indwelling needle 10 serving as an outer needle unit, for example, and by an inner needle unit including an inner needle having a needle tip being inserted through the outer needle unit. Alternatively, by the cannula 12 comprising a hollow needle made of metal or the like having a needle tip, the hemostasis valve-equipped indwelling needle 10 can be directly stuck into the patient's blood vessel and indwelled there.

Figure 9:
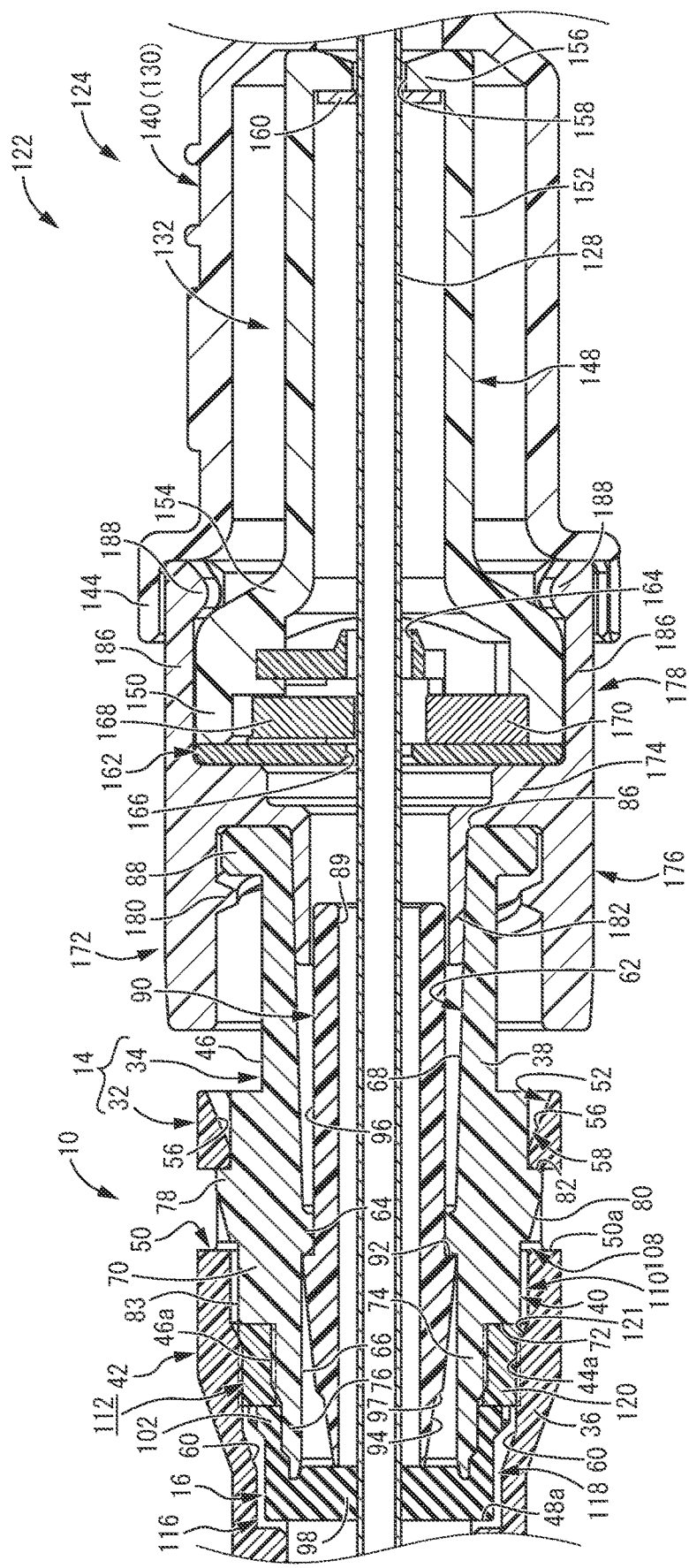
FIG. 9 is an enlarged vertical cross sectional view of a principal part in FIG. 8.

FIGS. 7 to 9 show a specific example of the indwelling needle assembly according to the present invention. An indwelling needle assembly 122 of the present practical embodiment is constituted by the hemostasis valve-equipped indwelling needle 10 serving as the outer needle unit, and an inner needle unit 124 is inserted through the internal flow path 18 of the outer needle unit 10 from the proximal end side toward the distal end side.

That is, the inner needle unit 124 includes an inner needle 128 having a sharp needle tip 126 at its distal end, an inner needle hub 130 attached to the proximal end of the inner needle 128, and a needle tip protector 132 mounted onto the inner needle 128 so as to be movable in the needle axis direction.

In the present practical embodiment, the inner needle 128 is a hollow needle, and is formed of a known material such as stainless steel, aluminum, titanium, and an alloy thereof. The needle tip 126 provided at the distal end of the inner needle 128 is provided with a blade surface 134 that is inclined with respect to the needle axis direction, so that puncture of a living body can be performed easily and with low stimulation. Large-diameter parts 136 having an enlarged outer diameter dimension are formed on the outer circumferential surface of the distal end portion of the inner needle 128. The large-diameter part 136 may be formed over the entire circumference in the circumferential direction by manufacturing the inner needle 128 by centerless process. However, in the present practical embodiment, the large-diameter parts 136 are formed in a pair on opposite sides in one diametrical direction (opposite sides in the vertical direction in FIG. 8) by the inner needle 128 being subjected to crushing process.

On the other hand, the inner needle hub 130 attached to the proximal end of the inner needle 128 has a structure in which a roughly cylindrical pedestal part 138 to which the proximal end of the inner needle 128 is fixed in an embedded state, a protector accommodation part 140 having a generally round tubular shape and protruding from the distal end of the pedestal part 138 with a larger outer diameter dimension than that of the pedestal part 138, and a generally round tubular coupling part 142 protruding from the proximal end of the pedestal part 138 are integrally formed of synthetic resin. In addition, a generally round tubular cap accommodation part 144 having an even larger diameter is formed at the distal end of the protector accommodation part 140.

Further, an inner needle cap 146 is removably assembled to the proximal end opening part of the coupling part 142. The inner needle cap 146 is a synthetic resin member having a roughly stepped round tubular shape provided with a step part at the middle portion in the needle axis direction. Note that a ventilation filter (not shown) is provided inside the inner needle cap 146, and the ventilation filter has a property that allows gas to pass through but blocks liquid. As such a ventilation filter, for example, the one formed of a material similar to that of the filter 120 provided on the air vent passage 118 inside the link connector 14 can be adopted. By assembling the inner needle cap 146 to the coupling part 142, the proximal end opening part of the inner needle hub 130 is liquid-tightly covered, so that blood return through the inner needle 128 does not leak to the outside. In addition, by the inner needle hub 130 and the inner needle cap 146 being made of transparent members, it is possible to easily confirm blood return (flashback).

The needle tip protector 132 of the inner needle unit 124 includes a generally round tubular protector main body 148. The protector main body 148 has a distal end portion that is larger in diameter than the proximal end portion, that is, the protector main body 148 includes a large-diameter tube part 150 on its distal end side, a small-diameter tube part 152 on its proximal end side, and a tapered tube part 154 that couples the large-diameter tube part 150 and the small-diameter tube part 152. Moreover, the proximal end opening part of this protector main body 148 (proximal end opening part of the small-diameter tube part 152) is closed off by a bottom wall 156 extending in the axis-perpendicular direction. A proximal needle through hole 158 that penetrates in the needle axis direction is formed at the center of the bottom wall 156, and a metal detaining ring 160 is fixed to the distal side end face of the bottom wall 156. The inner diameter dimensions of the proximal needle through hole 158 and the detaining ring 160 are smaller than the outer diameter dimensions of the large-diameter parts 136, 136 of the inner needle 128, while being larger than the outer diameter dimension of the portion other than the large-diameter parts 136, 136 of the inner needle 128.

On the other hand, the distal end opening part of the protector main body 148 (distal end opening part of the large-diameter tube part 150) is closed off by a lid body 162 having a roughly flat plate shape overall being assembled thereto. An intermediate needle through hole 164 is formed so as to penetrate the proximal end side of the lid body 162 in the needle axis direction, while a distal needle through hole 166 is formed so as to penetrate the distal end side thereof in the needle axis direction. The intermediate needle through hole 164 and the distal needle through hole 166 are provided with a predetermined remote distance from each other in the needle axis direction. The inner diameter dimensions of the intermediate needle through hole 164 and the distal needle through hole 166 are larger than the outer diameter dimensions of the large-diameter parts 136, 136 of the inner needle 128. Also, the length dimension in the needle axis direction from the proximal needle through hole 158 to the intermediate needle through hole 164 is roughly equal to or larger than the length dimension from the large-diameter parts 136, 136 to the needle tip 126 in the inner needle 128. The proximal end side beyond the large-diameter parts 136, 136 of the inner needle 128 is inserted through the proximal needle through hole 158, the intermediate needle through hole 164, and the distal needle through hole 166 in the needle tip protector 132, so that the needle tip protector 132 is externally mounted onto the inner needle 128 so as to be movable in the needle axis direction.

In addition, a shielding member 168 and a fixing member 170 are provided on the distal end side of the intermediate needle through hole 164 in the lid body 162, and the shielding member 168 and the fixing member 170 are accommodated in the large-diameter tube part 150 of the needle tip protector 132. The shielding member 168 and the fixing member 170 are each formed in a block shape and are provided on opposite sides of the inner needle 128 in an axis-perpendicular direction. Namely, the shielding member 168 is provided above the inner needle 128 in FIGS. 8 and 9, while the fixing member 170 is provided below the inner needle 128 in FIGS. 8 and 9. Further, the shielding member 168 can be displaced in the axis-perpendicular direction, whereas the fixing member 170 is fixedly attached to the lid body 162. One of the shielding member 168 and the fixing member 170 is a magnet, and the other is a ferromagnetic material such as a magnet and iron, and a magnetic attractive force is exerted on each other. Thus, the urging force that approaches the fixing member 170 is constantly applied to the shielding member 168, and the displacement of the shielding member 168 in the direction of approaching the fixing member 170 is limited by contacting the inner needle 128.

The protector main body 148 and the lid body 162 can be suitably formed of, for example, a rigid synthetic resin.

The proximal end of the inner needle 128 having the above-described structure is inserted into the pedestal part 138 of the inner needle hub 130 and subjected to bonding or welding as necessary, whereby the inner needle 128 is fixed to and supported by the inner needle hub 130. Besides, the needle tip protector 132 is mounted externally about the inner needle 128, whereby the inner needle unit 124 of the present practical embodiment is constituted. Then, the inner needle 128 protruding toward the distal end side in the inner needle unit 124 is inserted from the proximal end opening part of the outer needle unit 10, that is, the proximal end opening part 86 of the guide connector 34, and penetrates the disc valve 16 and the cannula 12, so that the needle tip 126 of the inner needle 128 protrudes from the distal end of the cannula 12.

Here, a connection cap 172 is provided between the guide connector 34 of the outer needle unit 10 and the needle tip protector 132 of the inner needle unit 124. The connection cap 172 has a roughly tubular shape overall, and a roughly annular middle wall 174 that protrudes radially inward is formed in its axially middle portion. That is, the connection cap 172 includes a coupling tube part 176 that opens to the distal end side with the middle wall 174 as a bottom wall, and an engaging tube part 178 that opens to the proximal end side with the middle wall 174 as a bottom wall.

A female thread 180 is formed on the inner circumferential surface of the coupling tube part 176, and can be screwed with the male thread provided on the outer circumferential surface of the flange part 88 in the proximal end opening part 86 of the guide connector 34. Further, on the radially inner side of the coupling tube part 176, a mating tube part 182 protrudes from the radially inner edge part of the middle wall 174 toward the distal end side. The outer diameter dimension of the mating tube part 182 is roughly equal to the inner diameter dimension of the proximal end opening part 86 of the guide connector 34, and the outer circumferential surface of the mating tube part 182 comprises a tapered surface roughly corresponding to the tapered surface 68 of the inner circumferential surface 62 of the guide connector 34. On the other hand, the inner diameter dimension of the mating tube part 182 is slightly larger than the outer diameter dimension of the proximal end portion of the pusher 90 (straight outer circumferential surface 96).

On the other hand, in the proximal end opening part of the engaging tube part 178, a pair of slits 184, 184 extending toward the distal end side are formed on each of both side portions in the one diametrical direction (both side portions in the vertical direction in FIGS. 8 and 9). These slits 184, 184 are remote from each other by a predetermined distance in the circumferential direction, and the portions circumferentially between these slits 184, 184, namely, the portions on opposite sides in the vertical direction in FIGS. 8 and 9, comprise flexible pieces 186, 186 that are flexurally deformable in the thickness direction (radial direction). Detaining claws 188, 188 that protrude radially inward are provided at the protruding ends (proximal ends in the axial direction) of the flexible pieces 186, 186 over roughly the entire length in the circumferential direction. The distance between the detaining claws 188, 188 in the direction of opposition (vertical distance in FIGS. 8 and 9) is made smaller than the outer diameter dimension of the large-diameter tube part 150 in the needle tip protector 132.

The connection cap 172 having the above-described structure is provided between the guide connector 34 and the needle tip protector 132, and by coupling these to each other, the outer needle unit 10 and the inner needle unit 124 are coupled to each other in the indwelling needle assembly 122.

That is, the mating tube part 182 of the connection cap 172 is inserted into the proximal end opening part 86 of the guide connector 34, and the female thread 180 provided on the inner circumferential surface of the coupling tube pan 176 is screwed with the male screw provided on the flange part 88, so that the connection cap 172 is coupled to the guide connector 34. In addition, the detaining claws 188, 188 of the flexible pieces 186, 186 provided on the engaging tube part 178 are detained to the tapered tube part 154 of the needle tip protector 132 from the radially outer side, so that the connection cap 172 and the needle tip protector 132 are coupled to each other. In the present practical embodiment, with the detaining claws 188, 188 detained to the tapered tube part 154, the distal side end face of the needle tip protector 132 (lid body 162) and the proximal side end face of the middle wall 174 of the connection cap 172 are in contact with each other. By the guide connector 34 and the needle tip protector 132 being coupled to each other via the connection cap 172 in this way, unintended detachment of the outer needle unit 10 from the inner needle unit 124 is prevented.

In the assembled state of the outer needle unit 10 and the inner needle unit 124, in the initial state, the small-diameter tube part 152 of the needle tip protector 132 is accommodated in the protector accommodation part 140 of the inner needle hub 130, while the proximal end of the connection cap 172 (engaging tube part 178) including the detaining claws 188, 188 is accommodated in the cap accommodation part 144 provided at the distal end of the protector accommodation part 140. That is, the flexible pieces 186, 186 are covered with the cap accommodation part 144 from the radially outer side, and the flexural deformation of the flexible pieces 186, 186 toward the radially outer side is prevented. By so doing, it can be prevented that the flexible pieces 186, 186 may unintentionally undergo flexural deformation toward the radially outer side and the detainment of the detaining claws 188, 188 to the tapered tube part 154 may be released.

The indwelling needle assembly 122 of the present practical embodiment constituted as described above is stuck into the patient's skin with the inner needle unit 124 inserted through the outer needle unit 10 as shown in FIGS. 7 to 9. Thereafter, by pulling out the inner needle unit 124 from the outer needle unit 10 to the proximal end side, the outer needle unit 10 is indwelled in a state of being percutaneously inserted into the blood vessel of the patient.

That is, when the inner needle 128 is pulled out to the proximal end side and the needle tip 126 of the inner needle 128 reaches the proximal end side with respect to the shielding member 168, the contact between the inner needle 128 and the shielding member 168 is released, so that the shielding member 168 is displaced in the direction of approaching the fixing member 170 due to the urging force. As a result, the shielding member 168 is displaced to be on the needle axis of the inner needle 128, so that the needle tip 126 of the inner needle 128 is protected by the needle tip protector 132.

Here, due to the inner needle hub 130 being displaced to the proximal end side with respect to the connection cap 172, the proximal end of the connection cap 172 is detached from the cap accommodation part 144, and the flexible pieces 186, 186 are allowed to undergo flexural deformation to the radially outer side. In this state, by pulling the inner needle 128 toward the proximal end, the large-diameter parts 136, 136 of the inner needle 128 and the detaining ring 160 (bottom wall 156) provided at the proximal end portion of the needle tip protector 132 are engaged, and due to the inner needle 128 being pulled out, the needle tip protector 132 is also displaced to the proximal end side with respect to the outer needle unit 10 and the connection cap 172 coupled to the outer needle unit 10. Due to the needle tip protector 132 moving to the proximal end side, the flexible pieces 186, 186 are flexurally deformed by the large-diameter tube part 150 of the needle tip protector 132 so as to be pushed to expand toward the radially outer side, thereby releasing the detainment of the detaining claws 188, 188 to the tapered tube part 154. As a result, the needle tip protector 132 is detached from the connection cap 172 while protecting the needle tip 126 of the inner needle 128, and the inner needle unit 124 is removed from the outer needle unit 10.

In addition, by providing the detaining ring 160 at the proximal end portion of the needle tip protector 132, the engagement force between the large-diameter parts 136, 136 of the inner needle 128 and the needle tip protector 132 can be improved. Further, when the needle tip protector 132 is pulled out to the proximal end side, the user can feel a relatively large pull-out resistance until the detaining claws 188, 188 get over the large-diameter tube part 150, and the pull-out resistance becomes roughly zero when the detaining claws 188, 188 get over the large-diameter tube part 150. Thus, the user can grasp that the needle tip protector 132 has been detached from the connection cap 172 only by the feeling of operation. That is, the inner needle unit 124 can be pulled out from the outer needle unit 10 with a good sense of clicking.

After the inner needle unit 124 is removed, the male thread part provided in the flange part 88 of the proximal end opening part 86 of the guide connector 34 and the female thread part provided on the inner surface of the coupling tube part 176 in the connection cap 172 are unscrewed, whereby the connection cap 172 is removed from the guide connector 34. As a result, the outer needle unit (hemostasis valve-equipped indwelling needle) 10 is indwelled in the patient's blood vessel in the state shown in FIGS. 1 to 3. By pulling out the inner needle unit 124 from the outer needle unit 10, the disc valve 16 elastically undergoes recovering deformation, and the slit 100 is closed. By so doing, in the indwelled state in the blood vessel, the internal flow path 18 of the hemostasis valve-equipped indwelling needle 10 is blocked by the disc valve 16.

Then, an external flow path such as a syringe is connected to the proximal end opening part (proximal end opening part of the guide connector 34) 86 of the link connector 14 in the hemostasis valve-equipped indwelling needle 10, whereby a male luer such as a syringe pushes the pusher 90 toward the distal end side, the central portion 98 of the disc valve 16 is pushed and expanded toward the distal end side while the slit 100 of the disc valve 16 is opened, so that the internal flow path 18 is brought into communication. Accordingly, infusion, blood collection, hemodialysis, and the like can be performed through the internal flow path 18 including the inner hole of the cannula 12, the inner hole of the elastic tube 28, and the inner hole 89 of the pusher 90.

Here, in a state where the hemostasis valve-equipped indwelling needle 10 is indwelled in the blood vessel of the patient, the space further on the distal end side than the disc valve 16 in the internal flow path 18 of the hemostasis valve-equipped indwelling needle 10 communicates with the external space through the air vent passage 118, whereby blood flows backward through the internal flow path 18 via the cannula 12 and the elastic tube 28. By the blood flowing backward through the internal flow path 18, the air in the internal flow path 18 is pushed out by the blood, and is configured to be discharged to the external space through the air vent passage 118. This makes it possible to prevent air remaining in the internal flow path 18 is mixed into the body when the external flow path is connected. It would also be acceptable that by the indwelling needle assembly 122 being stuck into the patient, blood flows backward through the passage hole 22 provided in the cannula 12 and the gap between the cannula 12 and the inner needle 128, that is, the discharge of air in the internal flow path 18 may be achieved before the inner needle unit 124 is pulled out.

In addition, since the filter 120 is provided on the air vent passage 118 to prevent the liquid from passing therethrough, blood leakage through the air vent passage 118 can be prevented. In particular, the filter 120 is sandwiched between the connector cover 32 and the guide connector 34 from inside and outside in the radial direction and mounted in a compressed state. Thus, even in the case where, for example, the hemostasis valve-equipped indwelling needle 10 is indwelled in an artery or the like and a relatively strong pressure such as arterial pressure is applied to the filter 120, deformation of the filter 120 is effectively suppressed, and the risk that a gap may be generated between the filter 120 and the connector cover 32 and/or the guide connector 34 can be reduced. This makes it possible to more reliably prevent the leakage of blood. Moreover, by the filter 120 being compressed, as to a sponge filter or the like, for example, the density of the filter 120 is increased and the air gap is reduced, so that the passage of blood can be more effectively prevented.

In the present practical embodiment, the air vent passage 118 is constituted by including the tunnel-like passages 116, 116, 116, 116 formed by the disc valve 16 covering the opening parts 114, 114, 114, 114 of the concave grooves 60, 60, 60, 60 in the inner circumferential surface 44 of the connector cover 32, and the gaps 108, 108, 110, 110 formed between the connector cover 32 and the guide connector 34. Thus, by assembling the connector cover 32, the guide connector 34, and the disc valve 16 together, the air vent passage 118 can be easily formed. In particular, by providing the inclined grooves 58, 58 and the notches 54, 54 to the connector cover 32, and providing the tubular support part 102 to the disc valve 16 and mounting so as to cover the guide connector 34, the assembly workability of the connector cover 32, the guide connector 34 and the disc valve 16 is improved. Accordingly, production efficiency of the link connector 14 having the air vent passage 118 inside, and hence the hemostasis valve-equipped indwelling needle 10 and the indwelling needle assembly 122 can be improved.

Figure 10:
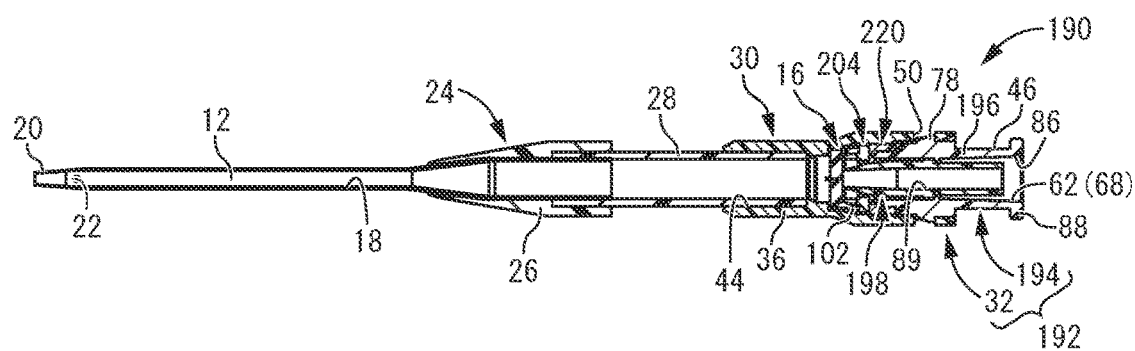
FIG. 10 is a perspective view of a hemostasis valve-equipped indwelling needle according to a second practical embodiment of the present invention.

FIG. 10 shows an hemostasis valve-equipped indwelling needle 190 as a second practical embodiment of the present invention. The hemostasis valve-equipped indwelling needle 190 includes a cannula 12 serving as a hollow needle on the distal end side thereof, and a link connector 192 to which an external flow path is connected on the proximal end side of the cannula 12. A disc valve 16 serving as a hemostasis valve is accommodated in the link connector 192. In the following description, members and portions that are substantially identical with those in the first practical embodiment are denoted by the same reference numerals in the drawings, and the description thereof is omitted.

The link connector 192 of the present practical embodiment has a shape in which a connector cover 32 and a guide connector 194, both of which have a generally round tubular shape, are coupled and fixed to each other in the axial direction. That is, the connector cover 32 is fixed to the distal end portion of the guide connector 194 by inserting and assembling the distal end side of the guide connector 194 into the proximal end side of the connector cover 32, and the link connector 192 is constituted.

Figure 11:
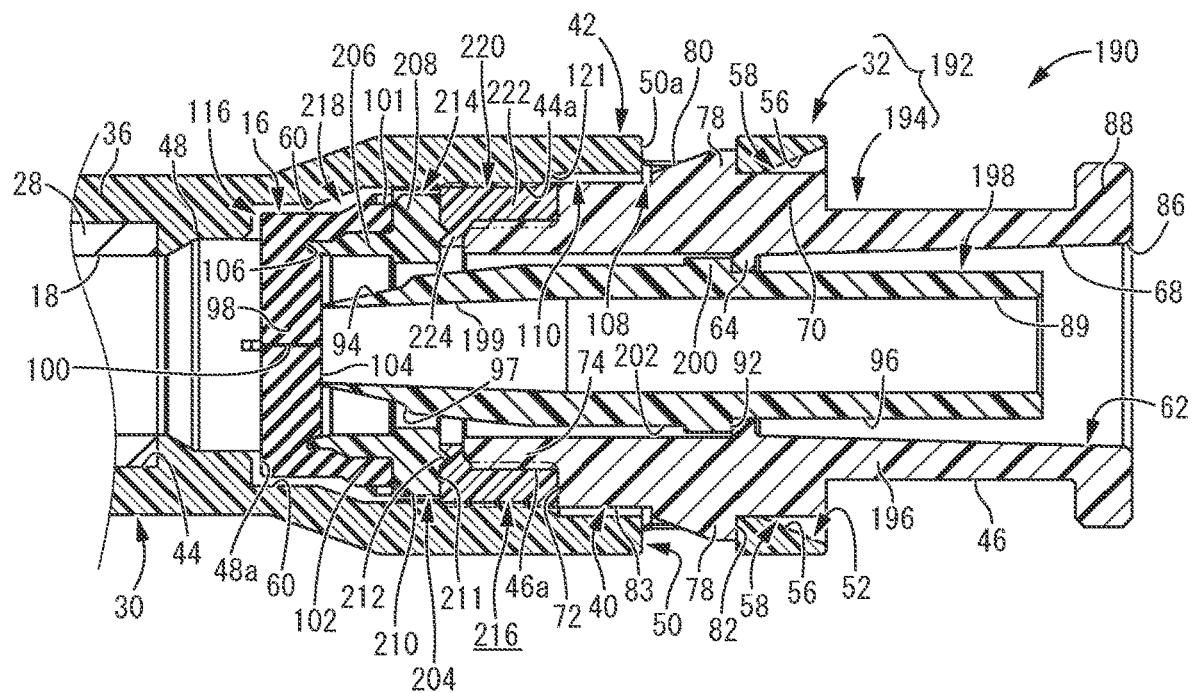
FIG. 11 is an enlarged vertical cross sectional view of a principal part in FIG. 10.

The guide connector 194 is formed of a rigid synthetic resin, and includes a circumferential wall 196 having a smaller diameter dimension than that of a circumferential wall 36 of the connector cover 32 as shown in FIG. 11. The circumferential wall 196 has a structure in which the insertion tube part 76 inserted into the tubular support part 102 of the disc valve 16 is omitted from the circumferential wall 38 of the preceding practical embodiment, and the inner diameter dimension is generally constant over roughly the entire length in the axial direction. On the other hand, the outer diameter dimension of the circumferential wall 196 changes in the axial direction.

A pusher 198 is disposed on the radially inner side of the guide connector 194. The pusher 198 has a tubular shape overall, and is provided with a flange-shaped projecting part 200 that protrudes outward at the axially middle portion thereof, so that a step surface 92 is formed by the proximal side end face of the projecting part 200. Moreover, the distal end portion of the pusher 198 is formed so as to become thinner toward the distal end side. Further, on the outer circumferential surface of the pusher 198, a straight outer circumferential surface 96 is set on the proximal end side of the projecting part 200, and a straight outer circumferential surface 202 is set on the distal end side of the projecting part 200 so as to extend with a roughly constant outer diameter dimension, and a tapered outer circumferential surface 94 is set further on the distal end side than the straight outer circumferential surface 202. Note that the maximum outer diameter dimension of the proximal end portion of the tapered outer circumferential surface 94 is roughly equal to the outer diameter dimension of the straight outer circumferential surface 202, and is larger than the outer diameter dimension of the straight outer circumferential surface 96.

The inner diameter dimension of the pusher 198 is roughly constant in the axial direction at the proximal end portion, and changes at the distal end portion so as to be smaller on the distal end side and to be larger on the proximal end side. In the present practical embodiment, an inner circumferential surface 199 at the distal end portion of the pusher 198 has a tapered shape that changes at a roughly constant change rate in the axial direction. With this configuration, it is possible to obtain a sufficient passage cross sectional area on the proximal end side of the pusher 198, as well as to make the radially innermost edge pressed against the disc valve 16 close to the center on the distal end surface of the pusher 198. As a result, it is possible to suppress the increase in the flow resistance of the fluid flow path (internal flow path) formed on the radial inside of the pusher 198 and obtain a small flow resistance, as well as to improve the ease in pushing open the disc valve 16.

Furthermore, with respect to the pusher 198, the distal end portion protrudes from the guide connector 194 toward the distal end side, and the distal end portion of the pusher 198 protruding from the guide connector 194 is inserted into the radially inner side of a valve support member 204. The valve support member 204 has a tubular shape overall, and is formed of a rigid synthetic resin, metal, or the like. Further, the valve support member 204 includes a tubular insertion tube part 206 and an annular mating part 208 that protrudes outward from the proximal end part of the insertion tube part 206. The insertion tube part 206 of the valve support member 204 has roughly the same shape as the insertion tube part 76 of the guide connector 34 in the first practical embodiment, and has an inner diameter dimension roughly the same as that of the guide connector 194, while its proximal end part protrudes radially inward so as to be partially reduced in diameter. Besides, in the mating part 208 of the valve support member 204, concave grooves 210, 210, 210, 210 that open to the outer circumferential surface are formed so as to penetrate in the axial direction at four locations arranged at equal intervals in the circumferential direction. Furthermore, an annular compression rib 212 that is continuous in the circumferential direction with a roughly constant cross-sectional shape projects from an axial end surface (proximal end surface) 211 on the proximal end side of the valve support member 204, and in the present practical embodiment, the compression rib 212 has a triangular cross section that becomes narrower in the radial direction toward the projecting tip.

With respect to the valve support member 204, the insertion tube part 206 is fitted into the tubular support part 102 of the disc valve 16, and the disc valve 16 is attached to the distal end portion of the valve support member 204. The valve support member 204 is inserted into the radial inside of the connector cover 32, and by the mating part 208 of the valve support member 204 being mated with the circumferential wall 36 of the connector cover 32, the valve support member 204 is fixed to the connector cover 32. By so doing, the disc valve 16 is accommodated in the radial inside of the connector cover 32 while being supported by the valve support member 204, and is positioned at a predetermined position in the radially inner space of the connector cover 32.

Moreover, the outer circumferential openings of the concave grooves 210, 210, 210, 210 provided in the mating part 208 of the valve support member 204 are covered with the connector cover 32, so that four gaps 214, 214, 214, 214 extending in the axial direction between the connector cover 32 and the valve support member 204 are formed by the concave grooves 210, 210, 210, 210.

Further, the distal end portion of the guide connector 194 is inserted into the connector cover 32 on the proximal end side of the valve support member 204. As in the first practical embodiment, the engaging projection 78 of the guide connector 194 is engaged with the inner surfaces of the engaging holes 50, 50 in the connector cover 32, so that the connector cover 32 and the guide connector 194 are coupled to each other. Besides, with respect to the pusher 198 disposed in the radial inside of the guide connector 194, the distal end portion protruding from the guide connector 194 is inserted in the radial inside of the valve support member 204, and its distal end is located on the proximal end side of the central portion 98 of the disc valve 16.

Additionally, a roughly annular accommodation region 216 is formed between the circumferential wall 36 of the connector cover 32 and the annular support part 74 of the guide connector 194. In the present practical embodiment, the guide connector 194 and the valve support member 204 are arranged so as to be axially spaced from and adjacent to each other, and the accommodation region 216 is opened to the radial inside axially between the distal end of the guide connector 194 and the proximal end of the valve support member 204. The accommodation region 216 communicates with the gaps 110, 110 located on the proximal end side of thereof and formed radially between the connector cover 32 and the guide connector 194, while communicating with the gaps 214, 214 located on the distal end side thereof and formed radially between the connector cover 32 and the valve support member 204.

As a result, the space in the internal flow path 18 further on the distal end side than the disc valve 16 communicates with the external space through the tunnel-like passages 116, 116, 116, 116, and the gaps 214, 214, 214, 214 between the connector cover 32 and the valve support member 204, the accommodation region 216, and the gaps 110, 110 as well as the gaps 108, 108 between the connector cover 32 and the guide connector 194. In other words, an air vent passage 218 that allows the space in the internal flow path 18 further on the distal end side (cannula 12 side) than the disc valve 16 to communicate with the external space is formed in the link connector 14 by including the tunnel-like passages 116, 116, 116, 116, the gaps 214, 214, 214, 214 between the connector cover 32 and the valve support member 204, the accommodation region 216, and the gaps 110, 110 as well as the gaps 108, 108 between the connector cover 32 and the guide connector 194. The air vent passage 218 communicates with the external space through the engaging holes 50, 50 serving as the air outlet port.

Here, a filter 220 is disposed in the accommodation region 216. Like the filter 120 of the first practical embodiment, the filter 220 has a property of allowing gas to pass through but does not allow liquid to pass through, and can be formed of the similar material to the filter 120 of the first practical embodiment. Further, the filter 220 of the present practical embodiment integrally includes a fitting part 222 that is externally fitted onto the guide connector 194, and an inside protrusion 224 that is disposed axially between the guide connector 194 and the valve support member 204. The fitting part 222 has a generally round tubular shape, and in the isolated state, its inner diameter dimension is smaller than the outer diameter dimension of the annular support part 74 of the guide connector 194, while its outer diameter dimension is larger than the inner diameter dimension of the circumferential wall 36 of the connector cover 32 that constitutes the wall portion of the accommodation region 216. The inside protrusion 224 protrudes from the distal end portion of the fitting part 222 toward the radial inside, and has an axial dimension that is approximately the same as or slightly larger than the distance between the axially opposed faces of the distal end surface of the guide connector 194 and the proximal end surface 211 of the valve support member 204.

With respect to the filter 220, the fitting part 222 is fitted externally about the distal end portion (annular support part 74) of the guide connector 194 with the inside protrusion 224 overlapped on the distal end surface of the guide connector 194, so that the filter 220 is attached to the guide connector 194. By the guide connector 194 being attached to the connector cover 32, the filter 220 is accommodated in the accommodation region 216 and disposed on the air vent passage 218. By the filter 220 being externally attached to the guide connector 194 in this way, the filter 220 can be handled integrally with the guide connector 194. This makes it possible to complete the arrangement of the filter 220 in the accommodation region 216 simultaneously with the assembly of the connector cover 32 and the guide connector 194, thereby facilitating the work of arranging the filter 220.

For example, after the valve support member 204 to which the disc valve 16 is mounted in advance is assembled to the connector cover 32, the guide connector 194 to which the pusher 198 and the filter 220 are mounted in advance is assembled to the connector cover 32, so that the link connector 192 is formed in a state in which the disc valve 16, the pusher 198 and the filter 220 are accommodated.

With respect to the fitting part 222 of the filter 220, in the isolated state before being assembled to the link connector 192, the thickness dimension is larger than the radial distance between the inner circumferential surface of the connector cover 32 that forms the wall surface of the accommodation region 216 and the outer circumferential surface of the guide connector 194. With this configuration, the fitting part 222 of the filter 220 is assembled to the link connector 192 in a state of being sandwiched and compressed in the radial direction between the connector cover 32 and the guide connector 194. In the present practical embodiment, the inner and outer rigid members that clasp the filter 220 in the radial direction are constituted by the connector cover 32 and the guide connector 194.

Further, with respect to the inside protrusion 224 of the filter 220, in the isolated state before being assembled to the link connector 192, the thickness dimension in the axial direction is larger than the axial distance between the protruding tip of the compression rib 212 of the valve support member 204 and the distal end surface of the guide connector 194. By so doing, the inside protrusion 224 of the filter 220 is assembled to the link connector 192 in a state of being sandwiched and compressed in the axial direction over the entire circumference by the guide connector 194 and the valve support member 204. In the present practical embodiment, the rigid members that clasp the filter 220 in the axial direction are constituted by the guide connector 194 and the valve support member 204. Besides, with the inside protrusion 224 clasped between the guide connector 194 and the valve support member 204, the inner diameter of the inside protrusion 224 is larger than the inner diameters of the guide connector 194 and the valve support member 204, and the filter 220 is configured so as not to project further inward than the guide connector 194 and the valve support member 204.

As described above, by the filter 220 being assembled to the link connector 192 in a compressed state at the fitting part 222 and the inside protrusion 224, roughly the entire filter 220 accommodated in the accommodation region 216 of the link connector 192 is in a compressed state, so that the filter 220 is stably positioned and held with respect to the link connector 192. In the present practical embodiment in particular, the rigid members that clasp the filter 220 are constituted by the connector cover 32 and the guide connector 194 that constitute the link connector 192, and the valve support member 204 that supports the disc valve 16. Thus, the rigid members can be provided without increasing the number of components.

With respect to the filter 220, the entire inside protrusion 224 may be sandwiched and compressed axially between the guide connector 194 and the valve support member 204, or the inside protrusion 224 may be partially sandwiched and compressed by the pressed portions of the compression rib 212 or the like. Similarly, the fitting part 222 may be radially sandwiched and compressed over the entire length in the axial direction, or may be partially sandwiched and compressed in the radial direction. In the structure of the present practical embodiment, the distal end portion provided to the inside protrusion 224 is located further on the distal end side than the guide connector 194, and thus may not be compressed in the radial direction. In addition, even if the axial dimension of the fitting part 222 of the filter 220 is smaller than the axial distance between the step surface 72 of the guide connector 194 and the proximal end surface 211 of the valve support member 204 in the isolated state, by the fitting part 222 being radially sandwiched and compressed between the connector cover 32 and the guide connector 194, for example, the fitting part 222 extends in the axial direction, so that the fitting part 222 can be pressed against both the step surface 72 and the proximal end surface 211. In short, it would be acceptable as long as the filter 220 is clasped by the connector cover 32, the guide connector 194, and the valve support member 204 in the arranged state in the accommodation region 216.

However, the description that the filter 220 is clasped between the rigid members does not necessarily mean that the filter 220 is sandwiched and supported between the rigid members in a compressed state only, but includes the case where, for example, the filter 220 is in contact with the rigid members with almost no gap therebetween (in a contact state without being compressed), and is sandwiched and supported by the rigid members in a roughly non-compressed state. In addition, when the filter 220 is a three-dimensional filtration structure (for example, a sponge filter or a sintered material) as exemplified in the practical embodiment, the filter 220 is sandwiched and supported in a compressed state in a direction orthogonal to the air flow, so that the passage of liquid from the filter 220 can be prevented extremely effectively. Furthermore, the filter 220 does not necessarily have to be supported only by clasping of the rigid members. For example, adhesion, welding or the like may be used together, or clasping of the rigid members may be realized via a soft member.

In the present practical embodiment, since the connector cover 32 and the guide connector 194 both have a tubular shape where the filter 220 is mounted, the fitting part 222 of the filter 220 is radially sandwiched and compressed over the entire circumference between the connector cover 32 and the guide connector 194. Moreover, since the guide connector 194 and the valve support member 204 both have a tubular shape where the filter 220 is mounted, the inside protrusion 224 of the filter 220 is axially sandwiched and compressed over the entire circumference between the guide connector 194 and the valve support member 204.

As in the preceding first practical embodiment, the hemostasis valve-equipped indwelling needle 190 according to the present practical embodiment having such a structure is used as an indwelling needle assembly by an inner needle unit (not shown) being inserted through the internal flow path 18, and is stuck into the patient's skin with an inner needle of the inner needle unit inserted through the cannula 12 serving as an outer needle. Thereafter, the inner needle unit is pulled out to the proximal end side from the hemostasis valve-equipped indwelling needle 190, which is an outer needle unit, so that the hemostasis valve-equipped indwelling needle 190 is indwelled with the cannula 12 percutaneously inserted in the blood vessel of the patient.

In this state where the hemostasis valve-equipped indwelling needle 190 is indwelled in the blood vessel of the patient, blood flows into the space of the internal flow path 18 further on the distal end side than the disc valve 16 through the cannula 12 and the elastic tube 28. Then, the blood flows backward through the internal flow path 18, so that the air in the internal flow path 18 further at the distal end side than the disc valve 16 is pushed out to the air vent passage 218 by the blood and discharged to the external space through the air vent passage 218.

In addition, the blood that has flowed back from the blood vessel into the internal flow path 18 cannot pass through the filter 220 disposed on the air vent passage 218, so that leakage of such blood to the external space through the air vent passage 218 is prevented.

In the present practical embodiment, the fitting part 222 of the filter 220 disposed on the air vent passage 218 is compressed in the radial direction between the connector cover 32 and the guide connector 194. Thus, the fitting part 222 of the filter 220 will more effectively prevent the blood from passing through, thereby making it difficult for blood to leak out to the external space.

Furthermore, since the inside protrusion 224 of the filter 220 is disposed between the guide connector 194 and the valve support member 204, the passage of blood to the radial inside is prevented by the inside protrusion 224, and blood is less likely to enter between the guide connector 194 or the valve support member 204 and the pusher 198, thereby preventing malfunction of the pusher 198 due to blood coagulation or the like.

Moreover, in the present practical embodiment, the compression rib 212 protrudes from the proximal end surface 211 of the valve support member 204, and by the compression rib 212 being more strongly pressed against the inside protrusion 224 of the filter 220, the inside protrusion 224 is greatly compressed in the axial direction. Therefore, between the guide connector 194 and the valve support member 204 in the axial direction, the filter 220 can be stably held by the compression of the inside protrusion 224, and the performance of preventing the blood from passing through by the filter 220 can be improved, thereby preventing the blood from passing to the radial inside. Note that it would be acceptable as long as the compression rib 212 is provided at a portion where the filter 220 is clasped in the axial direction, and the compression rib 212 may be provided so as to protrude from the distal end surface of the guide connector 194 to the distal end side, for example.

Further, the connector cover 32, the guide connector 194, and the valve support member 204 that clasp the filter 220 all have a tubular shape, and the filter 220 is clasped continuously over the entire circumference between the connector cover 32 and the guide connector 194, and between the guide connector 194 and the valve support member 204. By so doing, the filter 220 is more stably held in a predetermined mounted state, thereby more effectively preventing blood from leaking to the external space and the radially internal space.

Figure 12:
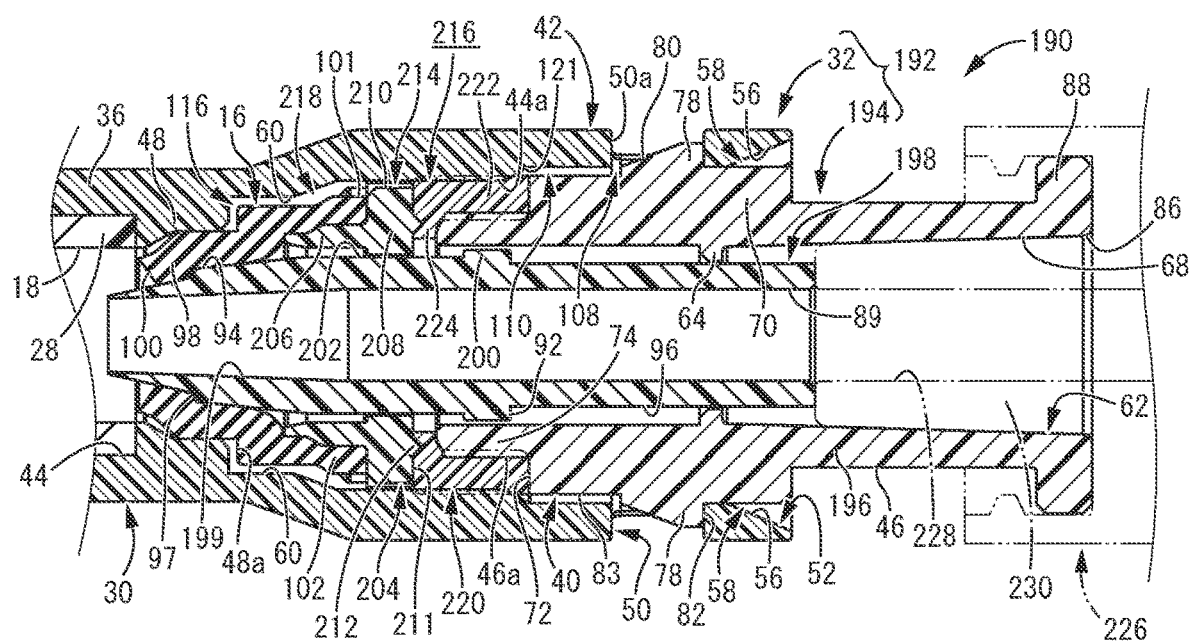
FIG. 12 is an enlarged vertical cross sectional view of a principal part in FIG. 10, showing a communicating state of an internal flow path.
Figure 13:
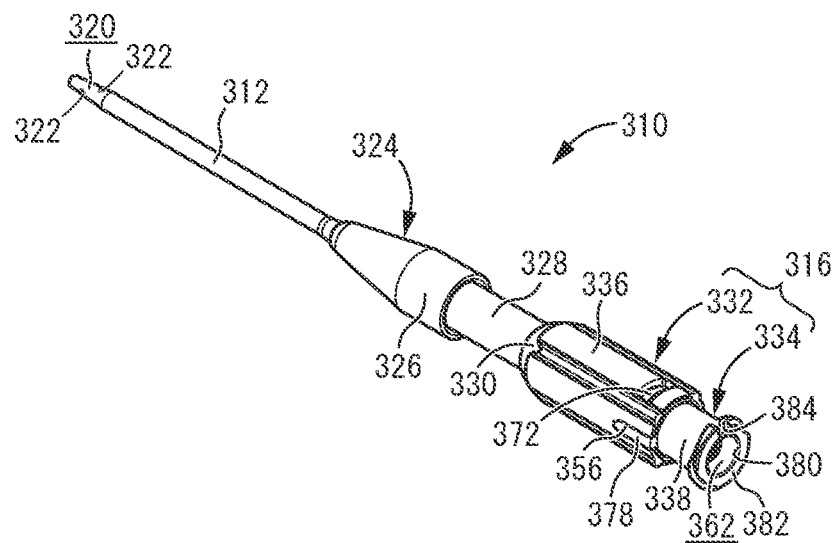
FIG. 13 is a view of a hemostasis valve-equipped indwelling needle according to a third practical embodiment of the present invention in a state prior to connection of an external flow path.

In addition, with respect to the hemostasis valve-equipped indwelling needle 190 indwelled in a patient's blood vessel, a syringe 226 or the like will be connected to the proximal end side thereof as in the first practical embodiment. That is, as shown in FIG. 12, an external flow path 228 of the syringe 226 is connected to the proximal end opening part 86 of the link connector 192 (proximal end opening part of the guide connector 194) in the hemostasis valve-equipped indwelling needle 190, so that a male luer 230 of the syringe 226 inserted into the guide connector 194 pushes the pusher 198 toward the distal end side, and the slit 100 of the disc valve 16 is opened while the central portion 98 of the disc valve 16 being expanded toward the distal end side by the pusher 198. By so doing, the internal flow path 18 of the hemostasis valve-equipped indwelling needle 190 communicates with the external flow path 228 of the syringe 226, so that infusion, blood collection, hemodialysis, and the like can be performed through the internal flow path 18 constituted by including the inner hole of the cannula 12, the inner hole of the elastic tube 28, and the inner hole 89 of the pusher 198.

FIGS. 13 to 16 show a hemostasis valve-equipped indwelling needle 310 as a third practical embodiment of the present invention. This hemostasis valve-equipped indwelling needle 310 includes a cannula 312 serving as a hollow needle on its distal end side, and on the proximal end side of the cannula 312, a needle hub housing (link connector) 316 serving as a housing in which a disc valve (hemostasis valve) 314 serving as an elastic valve body is accommodated. An internal flow path 318 is constituted by including the insides of the cannula 312 and the needle hub housing 316. By the cannula 312 being percutaneously inserted into a patient's blood vessel and indwelled therein, infusion or blood collection is performed through the internal flow path 318. Also, due to the external flow path being connected to and removed from the needle hub housing 316, opening and closing of the disc valve 314, that is, communication and blocking of the internal flow path 318 are switched. In the following description, the axial direction refers to the left-right direction in FIG. 14, which is the central axis direction of each member, and roughly corresponds to the needle axis direction of the cannula 312 that is a hollow needle, and which is the length direction. Further, the distal end side refers to the left side in FIG. 14 which is the side where the cannula 312 is stuck, while the proximal end side refers to the right side in FIG. 14 which is the side operated by the user.

More specifically, the cannula 312 is formed of a soft synthetic resin in the present practical embodiment, and the outer circumferential surface of the distal end portion constitutes a tapered outer circumferential surface 320 whose outer diameter dimension gradually decreases toward the distal end side. A plurality of passage holes 322 are formed in the circumferential wall of the distal end portion of the cannula 312 so that blood or the like can easily flow into the cannula 312 through the passage hole 322. In addition, the material of the cannula 312 is not limited to a soft synthetic resin, but may be a metal, for example.

The proximal end portion of the cannula 312 is fixedly supported by a needle hub 324. The needle hub 324 includes a roughly tubular circumferential wall 326, and is formed of, for example, a rigid synthetic resin. Then, the cannula 312 is inserted into the needle hub 324 and the proximal end portion of the cannula 312 is fixed to the needle hub 324 by adhesion or welding, so that the cannula 312 extends from the needle hub 324 to the distal end side.

An elastic tube 328 is connected to the proximal end side of the needle hub 324. The elastic tube 328 is formed of, for example, soft synthetic resin, and the distal end portion of the elastic tube 328 is sandwiched between the circumferential wall 326 of the needle hub 324 and the cannula 312 at the proximal end opening part of the needle hub 324, and subjected to bonding or welding as necessary. Accordingly, the elastic tube 328 is connected to the proximal end side of the needle hub 324. By so doing, the cannula 312 and the elastic tube 328 are firmly fixed to the needle hub 324.

The proximal end portion of the elastic tube 328 is fixed to the distal end portion of the needle hub housing 316. The needle hub housing 316 has a generally tubular shape overall. The proximal end portion of the elastic tube 328 is inserted from the distal end opening part of the needle hub housing 316 and is subjected to bonding or welding as necessary. By so doing, the elastic tube 328 and the needle hub housing 316 are connected to each other. That is, the distal end portion of the needle hub housing 316 constitutes a tube connecting part 330 to which the elastic tube 328 is connected. It can be understood that the needle hub is constituted by including the needle hub 324, the elastic tube 328, and the needle hub housing 316, and it can also be grasped that the needle hub housing 316 is one member constituting the needle hub. However, the elastic tube 328 is not essential, but the cannula 312 may extend from the distal end portion of the needle hub housing 316.

The internal flow path 318 extending from the cannula 312 to the needle hub housing 316 is constituted by including the inner holes of the cannula 312, the elastic tube 328, and the needle hub housing 316 (particularly, a pusher 396 described later provided inside the needle hub housing 316).

The needle hub housing 316 of the present practical embodiment has a shape including an outside housing (connector cover) 332 and an inside housing (guide connector) 334 both having a generally round tubular shape, the outside housing 332 being placed externally about the inside housing 334 so as to be fixed to each other. That is, the outside housing 332 is fixed in an axially coupled state to the distal end portion of the inside housing 334 by inserting and assembling the distal end side of the inside housing 334 to the proximal end side of the outside housing 332, and the needle hub housing 316 is constituted. Thus, the circumferential wall of the needle hub housing 316 is constituted by a circumferential wall 336 of the outside housing 332 and a circumferential wall 338 of the inside housing 334. In addition, the distal end portion of the circumferential wall 338 of the inside housing 334 that is inserted into the outside housing 332 comprises an insertion part 340 having a generally round tubular shape. On the other hand, the proximal end portion of the circumferential wall 336 of the outside housing 332, into which the insertion part 340 of the inside housing 334 is inserted, comprises an insertion target part 342 having a generally round tubular shape. The insertion part 340 and the insertion target part 342 may be provided opposite to each other, and the proximal end portion of the inside housing 334 may be inserted into the outside housing 332 located on the proximal end side.

The proximal end of the inside housing 334 extends further to the proximal end side with a predetermined axial dimension than the outside housing 332. Therefore, the circumferential wall of the needle hub housing 316 has a double wall structure at the portion where the insertion part 340 is inserted into the insertion target part 342, which is the coupling portion of the outside housing 332 and the inside housing 334. Meanwhile, the circumferential wall on the distal end side of the needle hub housing 316 is constituted by the circumferential wall 336 of the outside housing 332, and the circumferential wall on the proximal end side of the needle hub housing 316 is constituted by the circumferential wall 338 of the inside housing 334. That is, a proximal end portion 344a on the inner circumferential surface 344 of the outside housing 332 (inner circumferential surface of the insertion target part 342) and a distal end portion 346a of the outer circumferential surface 346 of the inside housing 334 (outer circumferential surface of the insertion part 340) are overlapped on each other, so that the outside housing 332 is placed externally about the inside housing 334 to form a double wall structure.

The outside housing 332 is made of a rigid synthetic resin and includes the roughly tubular circumferential wall 336. On the inner circumferential surface 344 in the axially middle portion of the circumferential wall 336, an annular wall part 348 is formed so as to protrude toward the radially inner side. The proximal end of the elastic tube 328 inserted from the distal end opening part of the outside housing 332 is in contact with the distal side end face of the annular wall part 348 extending in the axis-perpendicular direction. Thus, the portion of the outside housing 332 further on the distal end side than the annular wall part 348 constitutes the tube connecting part 330 to which the elastic tube 328 is connected. In addition, the proximal side end face of the annular wall part 348 extends in the axis-perpendicular direction, whereby an annular step surface 349 is formed on the inner circumferential surface 344 of the outside housing 332.

In the outside housing 332, the inner diameter dimension of the tube connecting part 330 which is the distal end side is roughly constant over roughly the entire length in the axial direction. In addition, the inner diameter dimension of the insertion target part 342 which is the proximal end side is slightly larger than that of the tube connecting part 330, and is roughly constant over roughly the entire length in the axial direction. In the present practical embodiment, on the inner circumferential surface 344 of the outside housing 332, the distal end portion of the insertion target part 342, namely, the portion which is adjacent on the proximal end side with respect to the annular wall part 348 is provided with a pressing rib 350 protruding toward the radially inner side. The pressing rib 350 is formed over the entire length in the circumferential direction or partially on the circumference.

Figure 14:
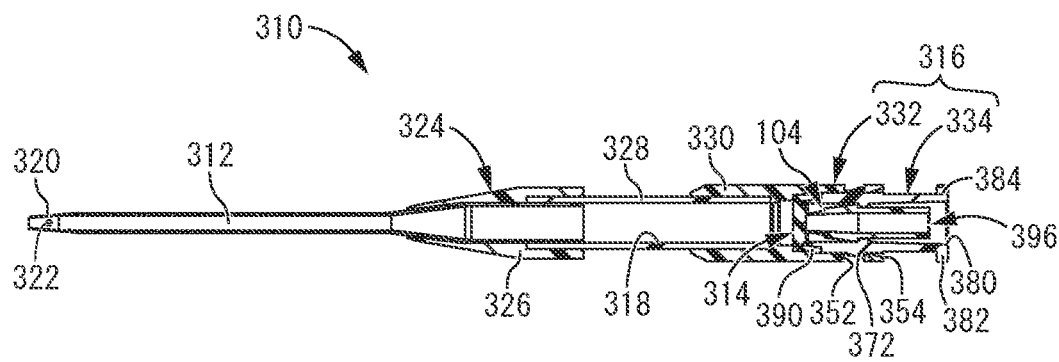
FIG. 14 is a vertical cross sectional view of the hemostasis valve-equipped indwelling needle shown in FIG. 13.
Figure 15:
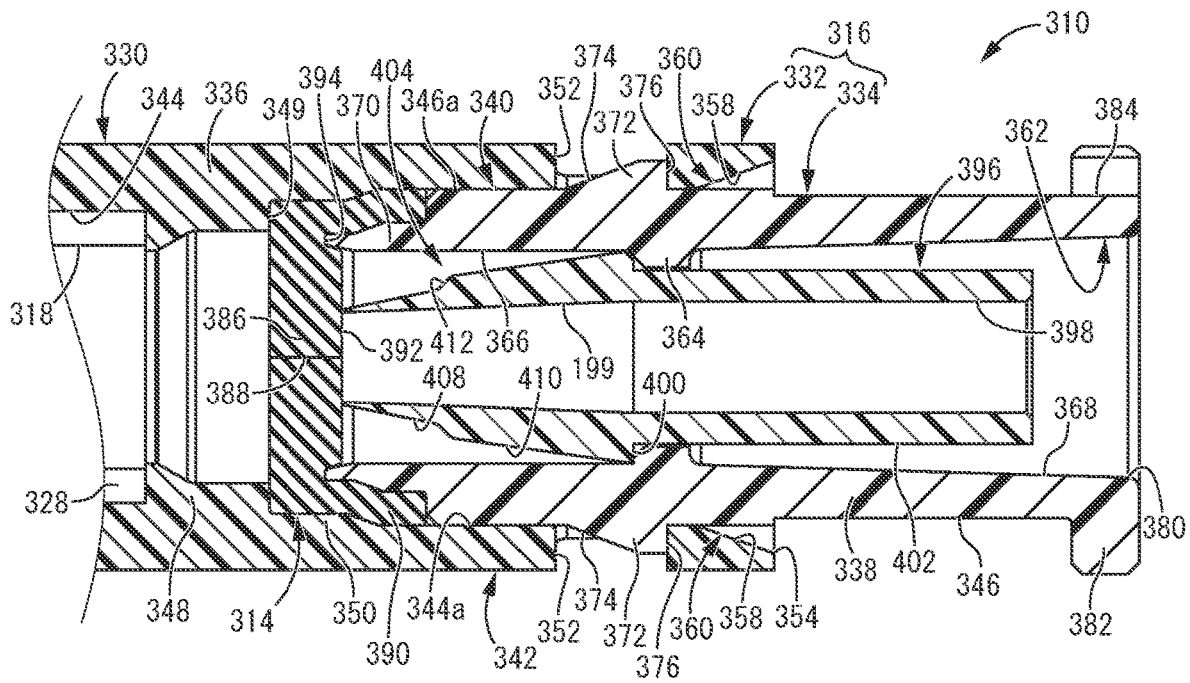
FIG. 15 is an enlarged vertical cross sectional view of a principal part in FIG. 14.
Figure 16:
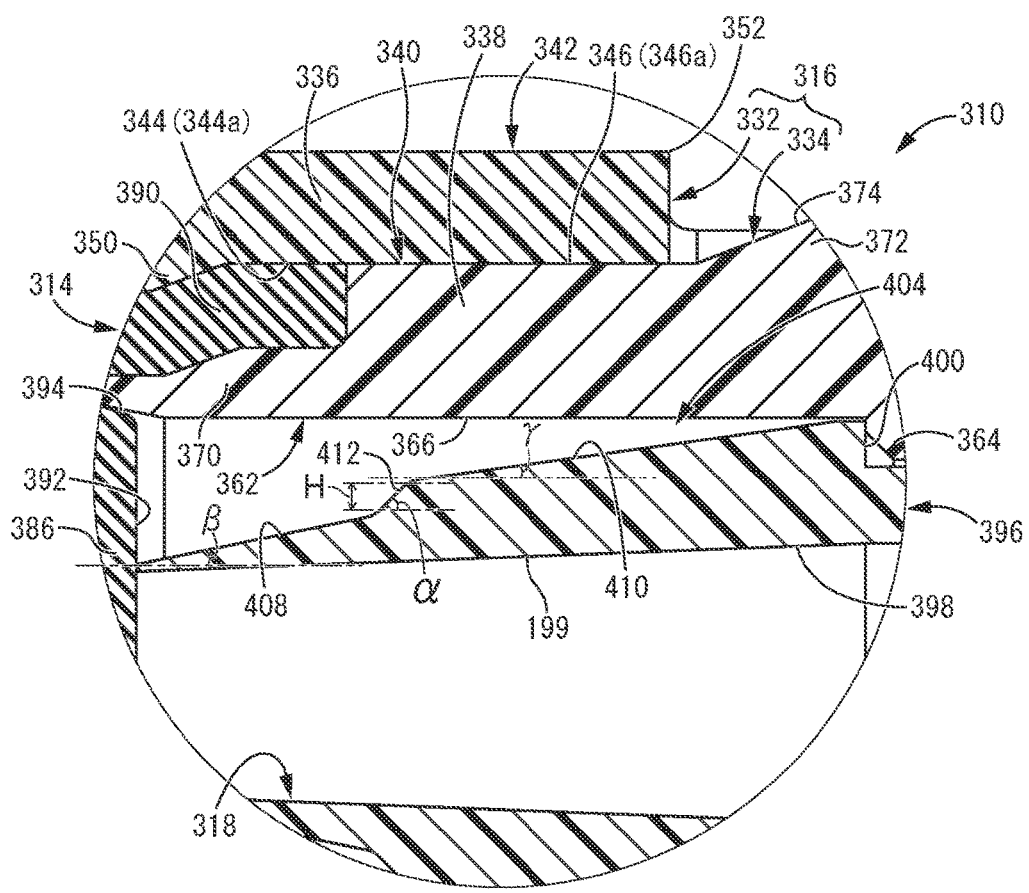
FIG. 16 is a further enlarged vertical cross sectional view of a principal part in FIG. 15.

Further, in the insertion target part 342 in the circumferential wall 336 of the outside housing 332, a pair of engaging holes 352, 352 penetrating the circumferential wall 336 in the thickness direction (radial direction) on opposite sides in one diametrical direction (opposite sides in the vertical direction in FIG. 14). Each of the engaging holes 352, 352 has a generally rectangular shape in a plan view, and is formed with a circumferential dimension that is less than ½ the circumference. Besides, in the circumferential wall 336 of the outside housing 332, at the location away from the pair of engaging holes 352, 352 in the circumferential direction, there are formed notches 356 extending from the opening edge of the proximal end opening part 354 toward the axially inner side (distal end side). In the present practical embodiment, a pair of notches 356, 356 are formed with a predetermined width dimension on opposite sides in the direction orthogonal to the direction of opposition of the pair of engaging holes 352, 352 (opposite sides in the front-rear direction of the paper surface in FIG. 14). The number of the notches 356 is not limited to two (a pair), but one or three or more may be provided on the circumference.

Furthermore, on the inner circumferential surface 344 of the insertion target part 342 of the outside housing 332, a pair of inclined surfaces 358, 358 are formed in the proximal end opening part 354. These inclined surfaces 358, 358 are formed in the same direction as the direction of opposition of the engaging holes 352, 352 (opposite sides in the vertical direction in FIG. 14), and the thickness dimension of the circumferential wall 336 gradually decreases toward the proximal end opening part 354. A pair of inclined grooves 360, 360 opened to the radially inner side are formed in the proximal end opening part 354 of the outside housing 332 by the inclined surfaces 358, 358 and the wall portions on both sides in the circumferential direction of the inclined surfaces 358, 358. In addition, the widthwise dimension of the inclined surfaces 358, 358 is roughly equal to the widthwise dimension of the engaging holes 352, 352, and the engaging holes 352, 352 and the inclined grooves 360, 360 are partially formed on the circumference at corresponding positions to each other in the circumferential wall 336 of the outside housing 332. That is, the engaging holes 352, 352 are formed on the distal end side of the inclined grooves 360, 360.

On the other hand, the inside housing 334 is formed of a rigid synthetic resin and includes the circumferential wall 338 having a smaller diameter than that of the circumferential wall 336 of the outside housing 332. The circumferential wall 338 has an inner diameter dimension and an outer diameter dimension that are roughly constant over roughly the entire length in the axial direction.

That is, on the inner circumferential surface 362 of the inside housing 334 (circumferential wall 338), an annular locking protrusion 364 is formed in the axially middle portion so as to protrude toward the radially inner side. In the inner circumferential surface 362 of the inside housing 334, the distal end side of the locking protrusion 364 comprises a guide surface 366 that guides the axial movement of a pusher 396 described later, and the inner diameter dimension thereof is roughly constant. On the other hand, the proximal end side of the locking protrusion 364 comprises a tapered surface 368 whose inner diameter dimension gradually increases toward the proximal end side.

Further, with respect to the distal end portion 346*a* of the outer circumferential surface 346 of the inside housing 334, that is, the outer circumferential surface 346*a* of the insertion part 340, the outer diameter dimension is reduced at the most distal end portion thereof. Accordingly, at the distal end portion of the inside housing 334, there is formed a generally round tubular support tube part 370 that protrudes toward the distal end side.

Furthermore, engaging projections 372 that project to the radially outer side are provided on the outer circumferential surface 346*a* of the insertion part 340. In the present practical embodiment, a pair of engaging projections 372, 372 are formed on opposite sides in one diametrical direction (opposite sides in the vertical direction in FIG. 14). The shape of the engaging projections 372, 372 in a plan view is a generally rectangular shape roughly corresponding to the engaging holes 352, 352 in the outside housing 332. And the distal side end faces of the engaging projections 372, 372 comprise inclined surfaces 374, 374 where the projecting height of the engaging projections 372, 372 gradually decreases toward the distal end side, while the proximal side end faces comprise vertical surface 376, 376 extending in the roughly axis-perpendicular direction. In addition, the inclination direction of the inclined surfaces 374, 374 of the engaging projections 372, 372 with respect to the axial direction is equal to the inclination direction of the inclined surfaces 358, 358 of the inclined grooves 360, 360 with respect to the axial direction. In the present practical embodiment, the inclination angles of the two inclined surfaces 358, 374 with respect to the axial direction are also roughly equal, and the inclined surface 358 and the inclined surface 374 are roughly parallel to each other in the axial direction. The number of the engaging projections 372 and the engaging holes 352 is not limited to two (a pair), but one or three or more may be provided on the circumference.

Further, on the outer circumferential surface 346*a* of the insertion part 340, on opposite sides in the direction orthogonal to the direction in which the pair of engaging projections 372, 372 are opposed to each other (opposite sides in the front-rear direction of the paper surface in FIG. 14), there are formed a pair of positioning projections 378, 378 having a shape roughly corresponding to the notches 356, 356 of the outside housing 332 so as to protrude therefrom.

In the inside housing 334, the proximal end side beyond the insertion part 340 extends roughly straight with an outer diameter dimension roughly equal to or slightly smaller than that of the insertion part 340, and on a proximal end opening part 380, there is formed a roughly annular flange part 382 protruding to the radially outer side. A male thread is formed on the outer circumferential surface of the flange part 382, so that a luer-lock type external flow path can be connected when an external flow path (syringe 414) to be described later is connected. In the present practical embodiment, a positioning concave groove 384 extending in the axial direction is formed in a part of the circumference of the flange part 382 (upper side in FIG. 14). Thus, for example, when the hemostasis valve-equipped indwelling needle 310 of the present practical embodiment serves as an outer needle unit and is used as an indwelling needle assembly in combination with an inner needle unit (not shown), by inserting a positioning convex part that protrudes to the distal end side from an inner needle hub constituting the inner needle into the positioning concave groove 384, relative rotation between the inner needle unit and the outer needle unit (hemostasis valve-equipped indwelling needle 310) will be prevented.

Here, the disc valve 314 is accommodated between the outside housing 332 and the inside housing 334 inside the needle hub housing 316. The disc valve 314 has a roughly disk shape and is formed of a material having elasticity such as rubber, elastomer, and the like. A slit 388 penetrating in the axial direction is formed in the central portion 386 of the disc valve 314. Although the shape of the slit 388 is not limited, in the present practical embodiment, the slit 388 has a radial shape extending roughly uniformly (approximately every 120 degrees) in three directions in the circumferential direction.

In addition, in the isolated state of the disc valve 314 before being assembled to the needle hub housing 316, the outer diameter dimension of the disc valve 314 is larger than the inner diameter dimension of the outside housing 332, particularly at the position where the pressing rib 350 is formed. By the disc valve 314 being assembled to the needle hub housing 316, a radial pressing force is exerted on the disc valve 314 by the pressing rib 350 from the radially outer side toward the radially inner side, so that the slit 388 is stably closed off. That is, the outer circumferential surface of the disc valve 314 is compressed to the radially inner side by the pressing rib 350 provided on the inner circumferential surface 344 (344a) of the outside housing 332.

A tubular support part 390 extending toward the proximal end side is provided on the outer circumferential portion of the disc valve 314. In addition, in the outer circumferential portion of a proximal end side surface 392 of the disc valve 314, on the radially inner side than the tubular support part 390, there is formed an annular circumferential groove 394 that continuously extends over the entire circumference in the circumferential direction and opens to the proximal end side. However, the tubular support part 390 is not essential. Further, the circumferential groove 394 is not essential, but the circumferential groove 394 may be formed by pushing the distal end of the support tube part 370 into the proximal end side surface 392 of the disc valve 314.

Here, on the radially inner side of the inside housing 334, a tubular pusher 396 is accommodated further on the proximal end side than the disc valve 314, and the center of the pusher 396 is penetrated by an inner hole 398 in the axial direction. On the outer circumferential surface of the pusher 396, there is formed a step surface 400 serving as an annular contact part that extends in the axis-perpendicular direction at the axially middle portion thereof. That is, the outer diameter dimension of the pusher 396 is such that the portion adjacent on the distal end side with respect to the step surface 400 has a larger diameter than the portion adjacent on the proximal end side with respect to the step surface 400, and the proximal end side of the step surface 400 comprises a straight outer circumferential surface 402 whose outer diameter dimension is roughly constant. On the other hand, the distal end side of the step surface 400 comprises a tapered outer circumferential surface 404 that gradually becomes smaller in diameter toward the distal end side, with the portion adjacent on the distal end side with respect to the step surface 400 having the maximum outer diameter.

With the pusher 396 of the present practical embodiment as well, similar to in the second practical embodiment, an inner circumferential surface 199 of the distal end portion of the pusher 396 has a tapered shape that decreases in diameter toward the distal end. Thus, it is possible to achieve both improvement in ease of pushing open the disc valve 314 and small flow resistance in the internal flow path.

In the present practical embodiment, as will be described later, the distal end side of the step surface 400 in the pusher 396, that is, roughly the entire formation part of the tapered outer circumferential surface 404 comprise an insertion region 406 (see FIG. 18) which is configured to be inserted into the disc valve 314 when the external flow path (syringe 414) is connected and the pusher 396 is moved to the distal end side. Specifically, in the present practical embodiment, the portion extending from the axially middle portion to the distal end side of a proximal end inclined surface 410 (described later) constituting the proximal end portion of the tapered outer circumferential surface 404 comprises the insertion region 406 to be inserted into the disc valve 314.

That is, in the present practical embodiment, the tapered outer circumferential surface 404 is formed in a tapered shape overall, and is constituted by including a distal end inclined surface 408 and a proximal end inclined surface 410 each having a tapered shape, and a taper-shaped steep-inclined surface 412 that connects these two inclined surfaces 408, 410 at the axially middle portion of the tapered outer circumferential surface 404 (insertion region 406). In short, on the tapered outer circumferential surface 404, the tapered distal end inclined surface 408 having a relatively small diameter is provided on the distal end side of the steep-inclined surface 412, and the tapered proximal end inclined surface 410 having a relatively large diameter is provided on the proximal end side of the steep-inclined surface 412. The distal end inclined surface 408, the proximal end inclined surface 410, and the steep-inclined surface 412 are annular tapered surfaces each extending over the entire circumference in the circumferential direction. Note that, by setting the diameter of the proximal end inclined surface 410 larger than that of the distal end inclined surface 408, in comparison with the case where only a single inclination angle (for example, the same angle as the distal end inclined surface 408) is set to the tapered outer circumferential surface as described in Patent Document 1, the sealing performance when the pusher 396 is inserted into the disc valve 314 can be improved.

The inclination angle $\alpha$ of the steep-inclined surface 412 with respect to the axial direction (see FIG. 16) is larger than the inclination angle $\beta$ of the distal end inclined surface 408 with respect to the axial direction (see FIG. 16) ($\theta<\alpha$). In the present practical embodiment, the inclination angle $\alpha$ is larger than the inclination angle $\gamma$ of the proximal end inclined surface 410 with respect to the axial direction (see FIG. 16) ($\gamma<\alpha$). In the present practical embodiment, the inclination angle $\beta$ of the distal end inclined surface 408 with respect to the axial direction is set to be not smaller than the inclination angle $\gamma$ of the proximal end inclined surface 410 with respect to the axial direction ($\gamma\leq\beta$). It should be noted that the inclination angle $\beta$ of the distal end inclined surface 408 and the inclination angle $\gamma$ of the proximal end inclined surface 410 may be equal to each other ($\beta=\gamma$), or the inclination angle $\gamma$ of the proximal end inclined surface 410 may be larger than the inclination angle $\beta$ of the distal end inclined surface 408 ($\beta<\gamma$).

Moreover, the inclination angles $\beta$, $\gamma$, $\alpha$ of the distal end inclined surface 408, the proximal end inclined surface 410, and the steep-inclined surface 412 are roughly constant in the axial direction. The distal end inclined surface 408 and the steep-inclined surface 412, as well as the steep-inclined surface 412 and the proximal end inclined surface 410 are connected by smooth curved surfaces. By so doing, roughly the entire tapered outer circumferential surface 404 is smoothly continuous. In addition, the distal end inclined surface 408 and the steep-inclined surface 412, and/or the steep-inclined surface 412 and the proximal end inclined surface 410 may be connected with a bend.

The inclination angles β, γ, α of the distal end inclined surface 408, the proximal end inclined surface 410, and the steep-inclined surface 412 are not limited at all, but as in the present practical embodiment, it would be preferable that the inclination angle α of the steep-inclined surface 412 is larger than the inclination angle β of the distal end inclined surface 408 and the inclination angle γ of the proximal end inclined surface 410 (β<α, γ<α). This is because, if the inclination angle α is smaller than the inclination angles β, γ (α<β, α<γ), the distal end inclined surface 408 and the proximal end inclined surface 410 whose inclination angles are made steep may not come into contact with the elastically deformed disc valve 314 depending on the insertion length of a male luer 416 of the syringe 414 described later into the needle hub housing 316. This makes it difficult to provide the structure in which the portion whose inclination angle is made steep is stably in contact with the disc valve 314, and there is a possibility that the effect of pushing back of the pusher 396 to the proximal end side, which will be described later, may not be stably exhibited.

Besides, it would be preferable that the inclination angles β, γ, α of the distal end inclined surface 408, the proximal end inclined surface 410, and the steep-inclined surface 412 are each set to a tapered shape, that is, within the range of 0 to 90 degrees. More preferably, the inclination angle β of the distal end inclined surface 408 and the inclination angle γ of the proximal end inclined surface 410 are each set within the range of 5 to 20 degrees, and in the present practical embodiment, are set to be β=γ=11.5 degrees. In particular, if the inclination angle γ of the proximal end inclined surface 410 exceeds 20 degrees, it would be undesirable because the axial dimension of the proximal end inclined surface 410, and hence of the insertion region 406 is shortened. Furthermore, the inclination angle α of the steep-inclined surface 412 is more preferably set within the range of 25 to 75 degrees, and even more preferably within the range of 35 to 60 degrees, and is set to 45 degrees in the present practical embodiment. This is because, if the inclination angle α of the steep-inclined surface 412 exceeds 75 degrees, the elastically deformed disc valve 314 and the steep-inclined surface 412 do not come into contact firmly and the contact area decreases, and there is a possibility that the effect of pushing back of the pusher 396 described later may not be sufficiently exhibited. By setting the inclination angles β, γ, α of the distal end inclined surface 408, the proximal end inclined surface 410, and the steep-inclined surface 412 within the above ranges, the effect of pushing back of the pusher 396 to the proximal end side, which will be described later, can be more stably obtained.

Furthermore, the axial dimensions of the distal end inclined surface 408, the proximal end inclined surface 410, and the steep-inclined surface 412 are not limited in any way either, but in the present practical embodiment, the steep-inclined surface 412 is provided slightly on the distal end side from the center of the tapered outer circumferential surface 404, that is, the axial dimension of the proximal end inclined surface 410 is larger than the axial dimension of the distal end inclined surface 408. In particular, in the present practical embodiment, in the insertion region 406, the axial dimension of the formation part of the steep-inclined surface 412 is 0.2 mm to 0.3 mm. Further, at least a part of the steep-inclined surface 412 is preferably located at a position of 1 mm to 3 mm from the distal end of the pusher 396, more preferably at a position of about 2 mm. In the present practical embodiment, the distal end of the steep-inclined surface 412 exists at a position of 1.7 mm from the distal end of the pusher 396. In short, the axial dimension of the formation part of the distal end inclined surface 408 is 1.7 mm. Moreover, the axial dimension of the formation part of the tapered outer circumferential surface 404 is preferably not less than 4 mm. By setting the axial dimension of each part in this manner, the elastically deformed disc valve 314 and the steep-inclined surface 412 can stably come into contact with each other even in the situation where external flow paths with various male luer lengths are circulating in the market as will be described later.

Additionally, the axis-perpendicular dimensions of the distal end inclined surface 408, the proximal end inclined surface 410, and the steep-inclined surface 412 are set according to the size of the pusher 396 and the disc valve 314, and are not limited in any way. For example, when the diameter dimension of the central portion 386 of the disc valve 314 (for example, the radially inner side of the circumferential groove 394) is 3.8 mm, the axis-perpendicular dimension H of the steep-inclined surface 412 (see FIG. 16) is preferably set within the range of 0.1 mm to 1.0 mm.

The needle hub housing 316 includes the outside housing 332 and the inside housing 334 having the above-described structure, and the disc valve 314 and the pusher 396 are accommodated inside the needle hub housing 316.

Specifically, the pusher 396 is inserted from the distal end opening part of the inside housing 334 and disposed. At that time, the proximal end position of the pusher 396 is determined by the locking protrusion 364 provided on the inner circumferential surface 362 of the inside housing 334 and the step surface 400 provided on the outer circumferential surface of the pusher 396 coming into contact with each other. In the accommodated state of the pusher 396, the straight outer circumferential surface 402 of the pusher 396 and the inner circumferential surface of the locking protrusion 364 are in contact with or slightly remote from each other, and the outer circumferential surface of the proximal end portion of the tapered outer circumferential surface 404 of the pusher 396 (proximal end portion of the proximal end inclined surface 410, that is, the maximum outer diameter portion of the tapered outer circumferential surface 404) and the guide surface 366 of the inside housing 334 are in contact with or slightly remote from each other. Accordingly, the pusher 396 is movable in the axial direction while being guided by the inner circumferential surface 362 of the inside housing 334.

The tubular support part 390 of the disc valve 314 is superposed on and supported by the distal end portion of the inside housing 334. That is, the distal end portion of the support tube part 370 that is the distal end of the inside housing 334 is inserted into the circumferential groove 394 provided on the proximal end side surface 392 of the disc valve 314. In the present practical embodiment, the inner and outer circumferential surfaces of the distal end portion of the support tube part 370 are in contact with or slightly remote from the inner and outer circumferential surfaces constituting the inner surface of the circumferential groove 394. A gap may be provided axially between the distal end surface of the support tube part 370 and the groove bottom surface of the circumferential groove 394.

The inner circumferential surface of the tubular support part 390 of the disc valve 314 is in contact with the outer circumferential surface of the support tube part 370, and the distal end portion of the inside housing 334 is fitted into the proximal end side of the disc valve 314. In the present practical embodiment, when the disc valve 314 is supported, the distal end of the pusher 396 is in contact with the proximal end side surface 392 of the disc valve 314, and the pusher 396 is positioned axially between the disc valve 314 and the locking protrusion 364. The distal end of the pusher 396 is not necessarily in contact with the proximal end side surface 392 of the disc valve 314, but the distal end of the pusher 396 and the proximal end side surface 392 of the disc valve 314 may be remote from each other in the axial direction.

The outside housing 332 is assembled from the distal end side of the disc valve 314. That is, the distal end portion of the inside housing 334 is inserted from the proximal end opening part 354 of the outside housing 332 with the disc valve 314 being superposed on and supported by the distal end thereof, and the engaging projections 372, 372 of the inside housing 334 are engaged with the engaging holes 352, 352 of the outside housing 332, so that the outside housing 332 and the inside housing 334 are coupled and fixed with the outside housing 332 being externally placed about the inside housing 334 while being in series in the axial direction on roughly the same central axis.

In the present practical embodiment, since the distal side end faces of the engaging projections 372, 372 comprise the inclined surfaces 374, 374, the engaging projections 372, 372 can be easily fitted into the engaging holes 352, 352. Further, since the proximal side end faces of the engaging projections 372, 372 comprise the vertical surfaces 376, 376, dislodgment of the engaging projections 372, 372 from the engaging holes 352, 352, that is, dislodgment of the inside housing 334 from the outside housing 332, is prevented.

In the present practical embodiment, at the proximal end opening part 354 of the outside housing 332, there are formed the inclined grooves 360, 360 constituted by including the inclined surfaces 358, 358. Thus, when the inside housing 334 is inserted into the outside housing 332, by the engaging projections 372, 372 being inserted into the inclined grooves 360, 360, relative rotation in the circumferential direction between the outside housing 332 and the inside housing 334 can be prevented. Further, since the engaging projections 372, 372 are stably guided to the engaging holes 352, 352 by the guiding action of the inclined surfaces 358, 358, the engaging projections 372, 372 can be more reliably engaged with the engaging holes 352, 352.

Furthermore, when the inside housing 334 is inserted into the outside housing 332, the positioning projections 378, 378 of the inside housing 334 are inserted into the notches 356, 356 provided in the proximal end opening part 354 of the outside housing 332. By so doing, the outside housing 332 and the inside housing 334 are easily positioned in the circumferential direction, so that the engaging projections 372, 372 can be even more reliably engaged with the engaging holes 352, 352.

In the assembled state of the outside housing 332 and the inside housing 334, the outer circumferential portion of the disc valve 314 is positioned in the axial direction and in the axis-perpendicular direction between the outside housing 332 and the inside housing 334 assembled to each other. By so doing, the disc valve 314 is assembled in a mated state of being mated with the outside housing 332 and the inside housing 334. That is, the outer circumferential portion of the disc valve 314 is clasped axially between the step surface 349 that is the proximal side end face of the annular wall part 348 provided in the outside housing 332 and the support tube part 370 that is the distal end portion of the inside housing 334. Further, the tubular support part 390 that protrudes to the proximal end side in the disc valve 314 is clasped radially between the circumferential wall 336 of the outside housing 332 and the support tube part 370 preferably in a compressed state. Moreover, the disc valve 314 is assembled so as to be compressed radially inward particularly by the pressing rib 350 of the circumferential wall 336 of the outside housing 332.

By coupling the cannula 312, the needle hub 324, the elastic tube 328, and the needle hub housing 316 including the disc valve 314 and the pusher 396 as described above in the axial direction, the hemostasis valve-equipped indwelling needle 310 according to the present practical embodiment is constituted. Such a hemostasis valve-equipped indwelling needle 310 is used as an indwelling needle assembly with a hemostasis valve by the hemostasis valve-equipped indwelling needle 310 serving as an outer needle unit, for example, and by an inner needle unit (not shown) including an inner needle having a needle tip being inserted through the outer needle unit. That is, after the outer needle unit (hemostasis valve-equipped indwelling needle) 310 is stuck into the patient's skin with the inner needle unit is inserted therein, the inner needle unit is pulled out from the outer needle unit 310 to the proximal end side, so that the outer needle unit 310 is indwelled while being percutaneously inserted in the patient's blood vessel. Alternatively, by the cannula 312 comprising a hollow needle made of metal or the like having a needle tip, the hemostasis valve-equipped indwelling needle 310 can be directly stuck into the patient's blood vessel and indwelled there. In the indwelled state in the blood vessel, the internal flow path 318 of the hemostasis valve-equipped indwelling needle 310 is blocked by the disc valve 314.

Figure 17:
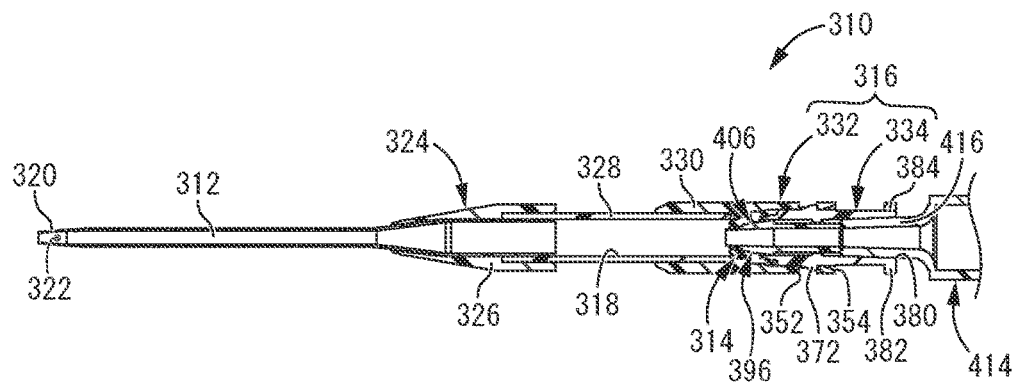
FIG. 17 is a vertical cross sectional view of the hemostasis valve-equipped indwelling needle shown in FIG. 13 with the external flow path connected.
Figure 18:
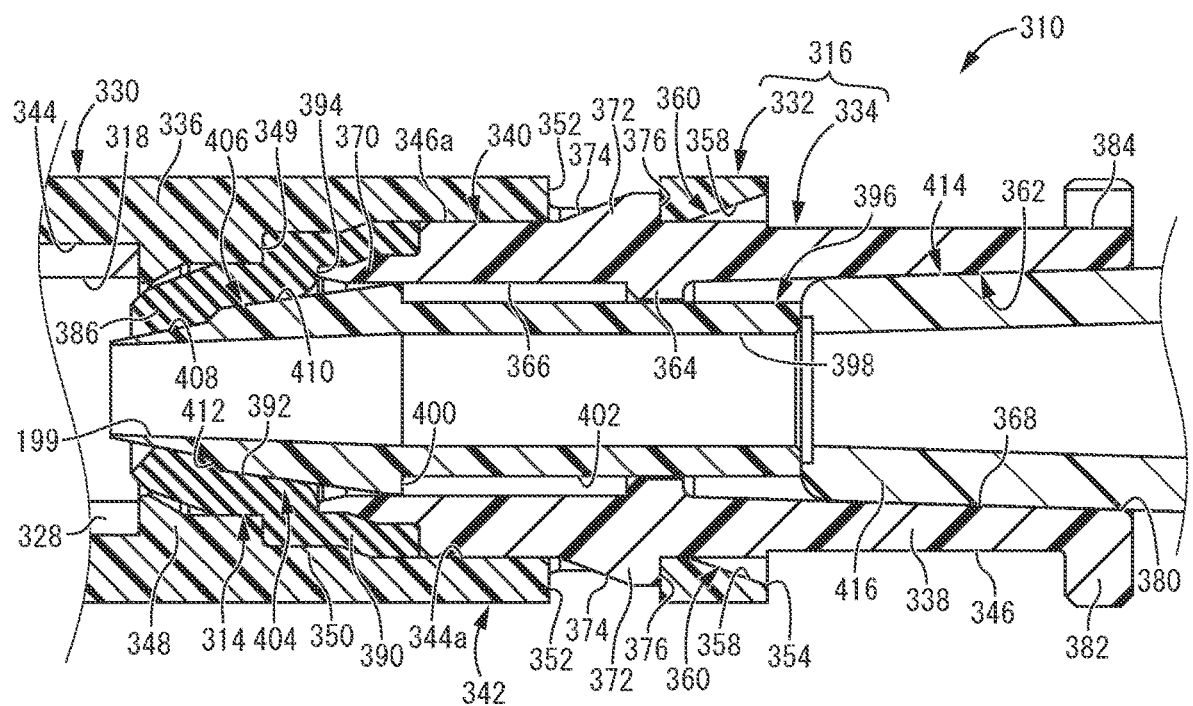
FIG. 18 is an enlarged vertical cross sectional view of a principal part in FIG. 17.

Then, for example, a syringe 414 is connected as an external flow path to the proximal end opening part (proximal end opening part of the inside housing 334) 380 of the needle hub housing 316 in the hemostasis valve-equipped indwelling needle 310. Accordingly, as shown in FIGS. 17 and 18, the male luer 416 such as the syringe 414 pushes the pusher 396 toward the distal end side, and the distal end portion of the pusher 396 is inserted into the disc valve 314, whereby the central portion 386 of the disc valve 314 is pushed and expanded to the distal end side while the slit 388 of the disc valve 314 is opened, so that the internal flow path 318 is brought into communication. Accordingly, infusion, blood collection, hemodialysis, and the like can be performed through the internal flow path 318 including the inner hole of the cannula 312, the inner hole of the elastic tube 328, and the inner hole 398 of the pusher 396.

On the other hand, when the infusion, blood collection, or hemodialysis is completed or interrupted, by removing the syringe 414 from the needle hub housing 316, the disc valve 314 is deformed so as to recover to its initial shape by the elastic recovering action of the disc valve 314. At the same time, the pusher 396 is pushed back by the disc valve 314 subjected to recovering deformation, so as to be moved to the proximal end side to the initial position shown in FIGS. 13 to 16. As a result, the slit 388 of the disc valve 314 is closed off, and the internal flow path 318 is blocked. In the present practical embodiment, the movement of the pusher 396 toward the proximal end side is restricted by contact of the step surface 400 provided on the outer circumferential surface of the pusher 396 and the locking protrusion 364 provided on the inner circumferential surface 362 of the needle hub housing 316 (inside housing 334).

Figure 19:
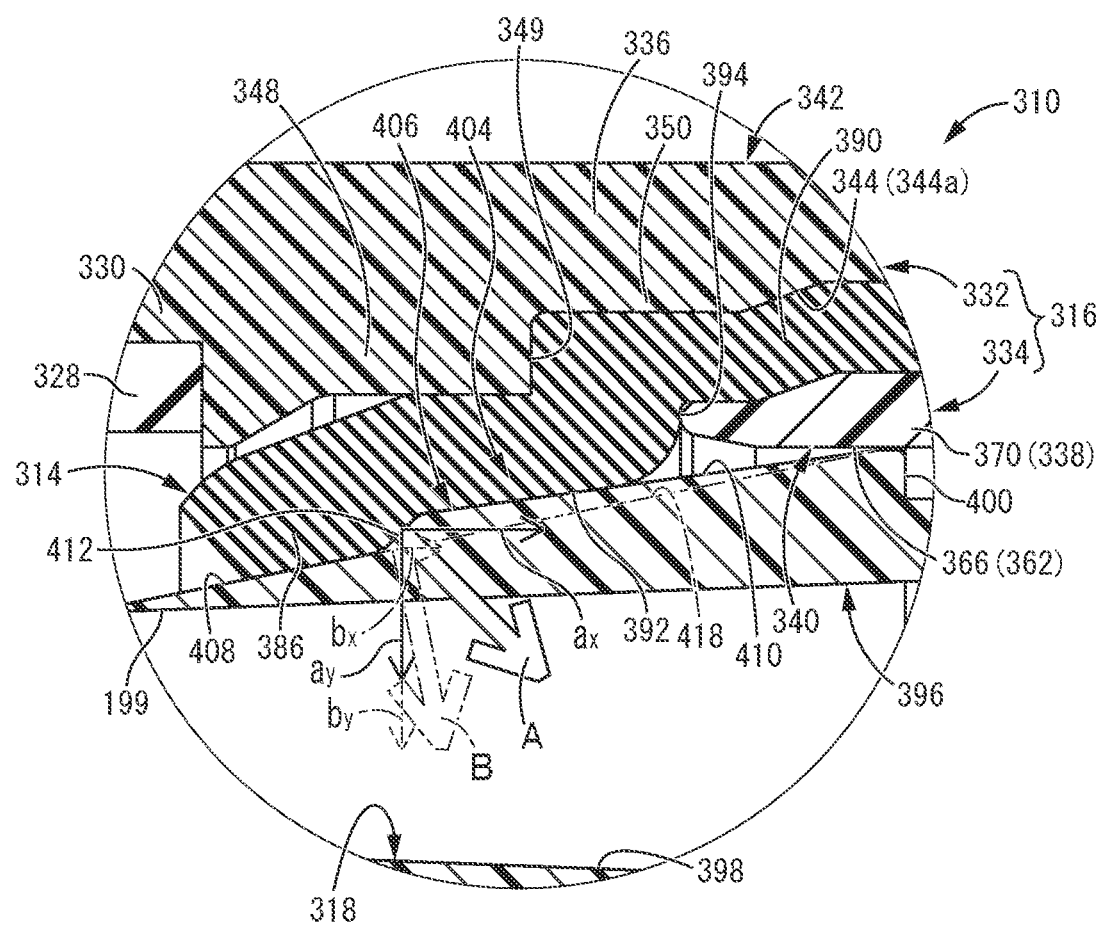
FIG. 19 is a further enlarged vertical cross sectional view of a principal part in FIG. 18.

Here, by the syringe 414 being connected from the proximal end opening part 380 of the needle hub housing 316 and the pusher 396 moving to the distal end side, the distal end portion of the pusher 396, particularly the portion extending from the axially middle portion of the proximal end inclined surface 410 to the distal end side thereof as shown in FIGS. 18 and 19 in the present practical embodiment, is configured to be inserted into the disc valve 314. That is, in the present practical embodiment, the portion extending from the axially middle portion of the proximal end inclined surface 410 to the distal end side thereof comprise the insertion region 406 to be inserted into the disc valve 314. Accordingly, the central portion 386 of the disc valve 314, which is elastically deformed to the distal end side due to the movement of the pusher 396 to the distal end side, comes into contact astride from the distal end inclined surface 408 to the proximal end inclined surface 410. Accordingly, as shown in FIG. 19, when the syringe 414 is connected (when the pusher 396 moves toward the distal end side), the elastic recovering force A of the disc valve 314 (illustrated by a white arrow in FIG. 19) is exerted on the steep-inclined surface 412. Whereas such an elastic recovering force is also exerted on the distal end inclined surface 408 and the proximal end inclined surface 410, illustration thereof is omitted.

The elastic recovering force A acts on the pusher 396 as a component force $a_x$ in the axial direction (shown by a fine line in FIG. 19) and a component force $a_y$ in the axis-perpendicular direction (shown by a fine line in FIG. 19). Thus, the pusher 396 is moved to the proximal end side in accordance with the component force $a_x$ in the axial direction due to removal of the syringe 414.

On the other hand, as in preceding Patent Document 1, for example, when assuming a virtual tapered outer circumferential surface 418 in which the tapered outer circumferential surface 404 of the distal end portion of the pusher 396 has only a single inclination angle, namely, as shown by a chain double-dashed line in FIG. 19, has the same inclination angle as the distal end inclined surface 408, the tapered outer circumferential surface 418 is subjected to an elastic recovering force B of the disc valve 314 (illustrated by a chain double-dashed line in FIG. 19). Such an elastic recovering force B acts on the pusher 396 as a component force $b_x$ in the axial direction (shown by a chain double-dashed line in FIG. 19) and a component force by in the axis-perpendicular direction (shown by a chain double-dashed line in FIG. 19). Therefore, as can be seen by comparing these component forces $a_x$ and $b_x$ in the axial direction, it is possible to increase the axial component in the elastic recovering force by providing the steep-inclined surface 412 having a large inclination angle on the tapered outer circumferential surface 404. In addition, the inclination angle of the tapered outer circumferential surface 418 having a single inclination angle, which is illustrated by a chain double-dashed line in FIG. 19, is 11.5 degrees.

That is, in the insertion region 406 of the pusher 396 into the disc valve 314, by providing the steep-inclined surface 412 having an inclination angle larger than the distal end inclined surface 408 (whose inclination angle is 11.5 degrees, for example), the elastic recovering force can more effectively act on the pusher 396 to the proximal end side. Thus, the pusher 396 can be moved more stably to the proximal end side when the syringe 414 is removed. Therefore, whereas the insertion region of the conventional structure (for example, Patent Document 2) has a single taper shape having only a single inclination angle, the hemostasis valve-equipped indwelling needle 310 according to the present invention has a novel configuration with respect to the point where the insertion region 406 is provided with the steep-inclined surface 412 having a larger inclination angle than that of the distal end side thereof.

In the present practical embodiment, since the distal end inclined surface 408 has a tapered shape, the inclination angle β of the distal end inclined surface 408 with respect to the axial direction is in the range of 0 to 90 degrees. That is, for example, when the amount of insertion of the male luer 416 of the syringe 414 into the needle hub housing 316, that is, the amount of movement of the pusher 396 toward the distal end side is small, the contact area between the disc valve 314 and the steep-inclined surface 412 is small. Therefore, the elastic recovering force of the disc valve 314 is small, and it is difficult for the pusher 396 to move to the proximal end side. However, by providing the distal end inclined surface 408 having the above-described inclination angle β and bringing the distal end inclined surface 408 and the disc valve 314 into contact when the pusher 396 moves to the distal end side, an effective axial component can be easily obtained from the elastic recovering force of the disc valve 314. By so doing, even when the amount of movement of the pusher 396 to the distal end side is small, the pusher 396 can be stably moved to the proximal end side due to the removal of the syringe 414.

Furthermore, in the present practical embodiment, since the proximal end inclined surface 410 has a tapered shape, the inclination angle γ of the proximal end inclined surface 410 with respect to the axial direction is in the range of 0 to 90 degrees. That is, for example, when the amount of insertion of the male luer 416 of the syringe 414 into the needle hub housing 316, that is, the amount of movement of the pusher 396 toward the distal end side is large, a larger recovering force of the disc valve 314 is required when pushing the pusher 396 back to the initial position. However, by providing the proximal end inclined surface 410 having the above-described inclination angle γ, an effective axial force can be obtained not only from the steep-inclined surface 412 but also from the proximal end inclined surface 410. By so doing, even when the amount of movement of the pusher 396 to the distal end side is large, the pusher 396 can be stably moved to the proximal end side due to the removal of the syringe 414.

That is, with the hemostasis valve-equipped indwelling needle 310 according to the present practical embodiment, regardless of whether the amount of insertion of the male luer 416 of the syringe 414 into the needle hub housing 316 is large or small, namely, regardless of the amount of insertion of the male luer 416 into the needle hub housing 316, the pusher 396 can be stably moved to the proximal end side. Incidentally, the length of the male luer 416 of the external flow path that can be connected to the hemostasis valve-equipped indwelling needle 310 currently distributed in the market is various, and it has been confirmed that there is a difference of 1.7 mm at the maximum. Here, in the present practical embodiment, the distal end of the steep-inclined surface 412 is provided at a position 1.7 mm from the distal end of the pusher 396. Thus, regardless of the length of the male luer 416, the disc valve 314 can be more reliably brought into contact with the steep-inclined surface 412, thereby stably obtaining a moving force for the pusher 396 toward the proximal end side.

In particular, as in the present practical embodiment, by setting the inclination angle β of the distal end inclined surface 408 to be larger than the inclination angle γ of the proximal end inclined surface 410, it is possible to obtain the effective moving force toward the proximal side as described above, while sufficiently obtaining the axial dimension of the proximal end inclined surface 410, and hence the axial dimension of the insertion region 406 to the disc valve 314. As a result, the pusher 396 can be more reliably inserted into the disc valve 314, thereby stably maintaining the communication state of the internal flow path 318.

The inclination angle α of the steep-inclined surface 412 with respect to the axial direction may be, for example, 90 degrees or not less than 90 degrees. However, as in the present practical embodiment, by providing a tapered shape, namely, setting the inclination angle α to be in the range of 0 degrees to 90 degrees, when the pusher 396 is moved to the distal end side (when the disc valve 314 is elastically deformed), the possibility that a gap is generated between the disc valve 314 and the steep-inclined surface 412 is reduced, thereby effectively exerting the elastic recovering force of the disc valve 314 on the steep-inclined surface 412. In particular, by making the inclination angle α of the steep-inclined surface 412 roughly constant in the axial direction, local unevenness is not formed, so that the possibility of generating a gap between the disc valve 314 and the steep-inclined surface 412 can be further reduced.

Further, by making the inclination angles β and γ of the distal end inclined surface 408 and the proximal end inclined surface 410 roughly constant in the axial direction, the possibility of generating a gap between the distal end inclined surface 408 and the disc valve 314, as well as between the proximal end inclined surface 410 and the disc valve 314 is also reduced. Therefore, the elastic recovering force of the disc valve 314 can be effectively exerted on the pusher 396 as a moving force toward the proximal end side.

Moreover, in the present practical embodiment, the locking protrusion 364 is provided on the inner circumferential surface 362 of the needle hub housing 316 (inside housing 334), and the step surface 400 serving as a contact part is provided on the outer circumferential surface of the pusher 396. By the locking protrusion 364 and the step surface 400 coming into contact with each other, the movement of the pusher 396 to the proximal end side is restricted. Accordingly, as in the present practical embodiment, even when the pusher 396 is easily moved to the proximal end side due to the elastic recovering action of the disc valve 314 at the time of removal of the syringe 414, dislodgment of the pusher 396 from the needle hub housing 316 can be effectively prevented.

Furthermore, in the present practical embodiment, the needle hub housing 316 is constituted by inserting the inside housing 334 into the outside housing 332. Since the disc valve 314 is supported between the inside housing 334 and the outside housing 332, the assembly of the needle hub housing 316 and the disc valve 314 can be facilitated. In particular, the tubular support part 390 of the disc valve 314 is sandwiched and supported in a compressed state radially between the outside housing 332 and the inside housing 334. Thus, even when the pusher 396 moves toward the distal end side, namely, even when the disc valve 314 is elastically deformed toward the distal end side, the disc valve 314 can be prevented from falling out of the needle hub housing 316.

Although the practical embodiments of the present invention have been described above, the present invention shall not be construed as limited to the specific descriptions in the practical embodiments, and may be embodied with various changes, modifications, improvements, and the like based on the knowledge of those skilled in the art.

For example, the inner needle unit constituting the indwelling needle assembly is not limited to the one described in the preceding practical embodiment, but a conventionally known inner needle unit including an inner needle and an inner needle hub can be adopted. That is, the shape of the needle tip protector is not limited to that in the preceding practical embodiment, either. However, in the indwelling needle assembly 122 according to the present invention, the needle tip protector 132 is not essential, and the connection cap 172 is not essential, either.

Besides, in the hemostasis valve-equipped indwelling needle 10 according to the present invention, the elastic tube 28 is not essential. That is, in the preceding practical embodiment, the cannula 12 is fixedly supported by the needle hub 24. However, the cannula 12 may be fixedly supported by the link connector 14, and in short, the link connector 14 may have the function of a needle hub.

Further, in the preceding practical embodiment, the concave groove 60 is provided on the inner circumferential surface 44 of the connector cover 32, and the opening part 114 of the concave groove 60 is covered with the disc valve 16, thereby forming the tunnel-like passage 116 constituting the air vent passage 118. However, the present invention is not limited to such an embodiment. That is, it would also be possible that the concave groove 60 is provided on the outer circumferential surface of the disc valve 16, and the opening part 114 of the concave groove 60 is covered with the inner circumferential surface 44 of the connector cover 32, thereby constituting the tunnel-like passage 116. Alternatively, it would also be possible that the concave grooves are provided on both the inner circumferential surface 44 of the connector cover 32 and the outer circumferential surface of the disc valve 16, and the tunnel-like passage is formed by the opening peripheral edges of the concave grooves being butted at each other. In the preceding practical embodiment, four (two pairs of) concave grooves 60, 60, 60, 60 are provided. However, the present invention is not limited such an embodiment. For example, one, two (a pair), three or more concave grooves may be provided, and the number thereof is not limited at all.

Moreover, in the first practical embodiment, the air vent passage 118 includes the tunnel-like passages 116, 116, 116, 116, and the gaps 108, 108, 110, 110 between the connector cover 32 and the guide connector 34, and the air in the internal flow path 18 further on the cannula 12 side than the disc valve 16 is discharged to the external space through the engaging holes 50, 50, but the present invention is not limited to such an embodiment. That is, the shape of the air vent passage 118, the opening position to the internal flow path 18 or the opening position to the external space is not limited at all. For example, a passage hole may be provided in the circumferential wall 36 of the connector cover 32, and the air vent passage may be constituted by the passage hole. In such a case, the filter is mounted in a compressed state in the passage hole. Further, the opening position of the air vent passage to the external space may be provided, for example, on the inner circumferential surface 62 of the guide connector 34, that is, the space on the distal end side of the disc valve 16 in the internal flow path 18 of the hemostasis valve-equipped indwelling needle 10 may communicate with the space further on the proximal end side than the disc valve 16 through the air vent passage. In such a case, air venting from the space on the distal end side of the disc valve 16 in the internal flow path 18 is achieved through the proximal end opening part 86 of the guide connector 34. It would also be possible to provide a plurality of mutually independent air vent passages in parallel.

Furthermore, in the first practical embodiment, the roughly annular accommodation region 112 is provided on the air vent passage 118 and the roughly tubular filter 120 is disposed in the accommodation region 112. However, the present invention is not limited to such an embodiment. That is, for example, when the accommodation region is divided in the circumferential direction to be semi-annular, the filter may be formed in a semi-tubular shape in accordance with the shape of the accommodation region. Thus, the shape of the filter 120 may be changed as appropriate in accordance with the shape of the air vent passage 118 or the accommodation region 112.

Additionally, in the first practical embodiment, the radial width dimension of the filter 120 before assembly is made larger than the radial dimension between the opposed faces of the connector cover 32 and the guide connector 34, and the filter 120 is compressed in the radial direction by being sandwiched radially between the connector cover 32 and the guide connector 34. However, the present invention is not limited to such an embodiment. That is, the radial width dimension of the filter 120 before assembly may be roughly equal to or slightly smaller than the radial dimension between the opposed faces of the connector cover 32 and the guide connector 34. Then, the filter 120 may be compressed in the radial direction by interposing another member radially between the connector cover 32 and the guide connector 34, for example. Alternatively, the filter 120 may be compressed axially between the disc valve 16 and the guide connector 34 so as to be expanded in the radial direction, thereby being compressed radially between the connector cover 32 and the guide connector 34.

Besides, in the preceding first practical embodiment, the link connector 14 is constituted by including the connector cover 32 and the guide connector 34, but the link connector may be constituted by a single member by an integrally molded product. Moreover, even if in the case where the link connector is constituted by several members like the preceding practical embodiment, these several members may be made into a mere tubular body, for example. Furthermore, in the preceding practical embodiment, the distal end portion of the guide connector 34 is inserted into the connector cover 32. However, for example, the proximal end portion of the connector cover 32 may be inserted into the guide connector 34. Alternatively, the proximal end opening part 52 of the connector cover 32 and the distal end opening part of the guide connector 34 may be butted at each other and fixed by adhesion, welding, or the like.

In the preceding practical embodiment, the air outlet port is constituted by the engaging holes 50, 50 used for positioning the connector cover 32 and the guide connector 34 (194). However, the air outlet port may be provided separately from the engaging holes 50, 50. For example, the air outlet port can be formed so as to open further on the distal end side than the engaging holes 50, 50 of the circumferential wall 36 of the connector cover 32.

The preceding practical embodiments described the example in which the rigid member that clasps the filter 120 (220) is constituted by the constituent member of the link connector 14 (192) or the valve support member 204 that supports the disc valve 16, but for example, it is also possible to provide the rigid member separately from the link connector 14 or the valve support member 204. Also, when a membrane filter in a thin film form is adopted, it would be conceivable to employ an annular rigid member that presses and clasps the outer circumferential end of the membrane filter against the connector cover. When the above structure is adopted, it is desirable that not only the outer circumferential end of the membrane filter is clasped between the rigid member and the connector cover, but also the outer circumferential end of the membrane filter is welded to at least one of the rigid member and the connector cover.

The first practical embodiment described the mode in which the filter 120 is sandwiched in the radial direction and mounted in a compressed state, while the second practical embodiment described the mode in which the filter 220 is sandwiched in the direction orthogonal to the direction in which the air flows (radial direction and axial direction) and mounted in the compressed state. However, the filter may be sandwiched and compressed in the direction inclined with respect to the radial direction and the axial direction. Further, for example, a non-annular, curving plate-shaped filter may be sandwiched and compressed in the circumferential direction of the hemostasis valve-equipped indwelling needle. In addition, in the case of using the membrane filter as described above, it is not essential that the filter is arranged in a compressed state in the direction orthogonal to the direction in which the air flows, and the filter may be mounted without being compressed because of its thin-film form.

Furthermore, the arrangement position of the filter is not limited to the aspect of the first practical embodiment or the second practical embodiment, but the filter can be arranged at an arbitrary position in the air vent passage provided in the link connector. Specifically, depending on the mode of the air vent passage, it is possible to arrange the filter in the air vent passage at any position, for example, on the radially outer side of the hemostasis valve, or the distal end side or the proximal end side of the hemostasis valve, in a compressed state in the radial direction or the axial direction, or in an uncompressed state.

The filter medium is not particularly limited, and various materials and structures can be adopted. For example, in addition to the three-dimensional filtration structure as exemplified in the preceding practical embodiment, a planar filtration structure such as a membrane filter can also be adopted. Besides, for example, it is possible that the filter carries a superabsorbent polymer that absorbs liquid, and it is possible that the filter is further provided with a function for preventing the liquid from passing through so that it would be more difficult for the liquid to pass through the filter. Furthermore, whereas a filter that allows gas to pass through but does not allow liquid to pass through is employed, it is not limited to a filter having perfect liquid-tightness in any state, as a matter of course. That is, the filter does not allow liquid to pass through easily, but there is a limit to the liquid impermeability of the filter. Therefore, if the liquid comes into contact with the filter with an excessively large pressure, the liquid can pass through the filter when the limit of liquid impermeability of the filter is exceeded.

Further, for example, in the third practical embodiment, the steep-inclined surface 412 is tapered, that is, the inclination angle $\alpha$ of the steep-inclined surface 412 with respect to the axial direction is set in the range of 0 degrees to 90 degrees. However, the inclination angle $\alpha$ of the steep-inclined surface 412 may be 90 degrees, or may be larger than 90 degrees. That is, when the inclination angle $\alpha$ of the steep-inclined surface 412 is 90 degrees, the steep-inclined surface 412 is a step-like surface extending in the axis-perpendicular direction. In the preceding practical embodiment, the distal end inclined surface 408 and the proximal end inclined surface 410 are also tapered, that is, the inclination angles $\beta$ and $\gamma$ of the distal end inclined surface 408 and the proximal end inclined surface 410 with respect to the axial direction are also set in the range of 0 degrees to 90 degrees. However, the inclination angles $\beta$ and $\gamma$ of the distal end inclined surface 408 and the proximal end inclined surface 410 may be 0 degrees. That is, the distal end side and/or the proximal end side of the steep-inclined surface 412 may be an annular surface that is not inclined with respect to the axial direction (parallel to the axial direction).

Moreover, in the preceding third practical embodiment, the inclination angles of the distal end inclined surface 408, the proximal end inclined surface 410, and the steep-inclined surface 412 are roughly constant in the axial direction. However, the present invention is not limited to such an embodiment, but for example, each of the inclined surfaces may be a curved surface whose inclination angle gradually changes in the axial direction. That is, for example, the tapered outer circumferential surface 404 provided at the distal end portion of the pusher 396 may be constituted by a curved surface whose inclination angle changes smoothly over roughly the entire length in the axial direction.

In the third practical embodiment, a single annular steep-inclined surface 412 is provided in the axially middle portion of the tapered outer circumferential surface 404. However, there may be provided a plurality of steep-inclined surfaces 412 that are remote from each other in the axial direction. That is, the distal end side and/or the proximal end side of the steep-inclined surface 412 may have a portion where the inclination angle changes by bending or curving. In short, one or a plurality of step-like surfaces extending in the axis-perpendicular direction may be provided on the distal end side and/or the proximal end side of the steep-inclined surface 412, and for example, the distal end portion of the pusher 396 may have a stairway shape that tapers roughly over its entirely. In such a case, it can be understood that a plurality of steep-inclined surfaces 412 extending in the axis-perpendicular direction are provided apart from each other in the axial direction, or it can be understood that a single steep-inclined surface 412 extending in the axis-perpendicular direction is provided, and the portion further on the distal end side thereof and the portion further on the proximal end side thereof each have a stairway shape.

In the third practical embodiment, whereas the needle hub housing 316 includes the outside housing 332 and the inside housing 334, the needle hub housing 316 may be integrally formed. Besides, even when separate members are assembled and fixed to each other, they need not be assembled by one member being inserted into the other member as in the preceding practical embodiment, but may be connected in series in the axial direction, for example. Moreover, the fixing means for the separated members is not limited to the engaging structure as in the preceding practical embodiment, but any conventionally known fixing means such as welding and adhesion can be adopted.

In the preceding third practical embodiment, whereas the distal end portion of the pusher 396 is constituted by the tapered outer circumferential surface 404 having a tapered shape overall, the present invention is not limited to such an embodiment. For example, there may be provided a protrusion including the steep-inclined surface 412 on the outer circumferential surface of the distal end portion of the pusher 396. However, it is not preferable that the disc valve 314 comes into contact with said protrusion from the proximal end side to prevent the pusher 396 from moving to the proximal end side.

In the third practical embodiment, in the tapered outer circumferential surface 404 of the pusher 396, the portion extending from the axially middle portion of the proximal end inclined surface 410 to the distal end side thereof comprises the insertion region 406 to be inserted into the disc valve 314. However, the present invention is not limited to such an embodiment, but it would be acceptable as long as the disc valve 314 elastically deformed toward the distal end side is configured to come into contact with the steep-inclined surface 412. That is, for example, the distal end side from the steep-inclined surface 412 may comprise the insertion region 406, and in the present invention, the shape on the proximal end side from the steep-inclined surface 412 is not limited at all.

In the pusher 396 of the third practical embodiment, the proximal end portion of the proximal end inclined surface 410 is positioned on the radially outer side of the straight outer circumferential surface 402, and the step surface 400 is formed between the proximal end inclined surface 410 and the straight outer circumferential surface 402. However, the step surface 400 is not essential, that is, for example, the steep-inclined surface 412 and the proximal end inclined surface 410 may be formed continuously from the distal end portion of the straight outer circumferential surface 402. However, the step surface 400 can be skillfully formed by making the proximal end portion of the proximal end inclined surface 410 project to the radially outer side of the straight outer circumferential surface 402. By combining the step surface 400 and the locking protrusion 364 provided on the inner circumferential surface 362 of the needle hub housing 316, a mechanism for restricting the movement of the pusher 396 to the proximal end side can be provided.

Further, on the outer circumferential surface of the pusher 396 according to the third practical embodiment, it is preferable to apply a lubricant to at least a portion with which the elastic valve body (disc valve 314) comes into contact (for example, the outer circumferential surface of the insertion region 406), and preferably to the steep-inclined surface 412 in particular. By so doing, the return of the pusher 396 to the proximal end side at the time of removal of the external flow path will be smooth. That is, in the pusher 396 according to the present invention, since the inclination angle of the steep-inclined surface 412 is large, the efficiency of the repulsive force by the elastic valve body acting in the direction of pushing back the pusher 396 inserted into the elastic valve body enhances, but frictional force increases. Therefore, by reducing the frictional force of the contact surface between the pusher 396 and the elastic valve body with a lubricant, it is possible to further improve the returnability of the pusher 396 to the proximal end side due to the recovering deformation of the elastic valve body. The concrete specifications such as the composition and viscosity of the lubricant to be employed may be appropriately selected according to the design of the pusher and the elastic valve body, and the method of attaching the lubricant to the pusher 396 is not limited. The lubricant is preferably applied to the outer circumferential surface of the pusher 396, but may be applied to the surface of the disc valve 314 in addition to or instead of the pusher 396.

KEYS TO SYMBOLS

10, 190, 310: hemostasis valve-equipped indwelling needle (outer needle unit), 12: cannula, 14, 192: link connector, 16, 314: disc valve (hemostasis valve, elastic valve body), 18: internal flow path, 32: connector cover (rigid member), 34, 194: guide connector (rigid member), 36: circumferential wall of connector cover, 44: inner circumferential surface of connector cover, 46: outer circumferential surface of guide connector, 50: engaging hole, 60: concave groove, 74: annular support part, 78: engaging projection, 89: inner hole (flow path constituting internal flow path), 108, 110, 214: gap, 114: opening part of concave groove, 116: tunnel-like passage, 118, 218: air vent passage, 120, 220: filter, 122: indwelling needle assembly, 128: inner needle, 204: valve support member (rigid member), 212: compression rib, 222: fitting part, 316 needle hub housing (housing, link connector), 332: outside housing (connector cover), 334: inside housing (guide connector), 364: locking protrusion (locking wall part), 390: tubular support part, 90, 396: pusher, 92, 400: step surface (contact part), 94, 404: tapered outer circumferential surface, 406: insertion region, 408: distal end inclined surface, 410: proximal end inclined surface, 97, 412: steep-inclined surface

The invention claimed is:

1. A hemostasis valve-equipped indwelling needle comprising:
   a cannula provided on a distal end side thereof and configured to be percutaneously inserted into a blood vessel;
   a link connector provided on a proximal end side thereof;
   an internal flow path extending from the cannula to the link connector; and
   a hemostasis valve disposed inside the link connector, wherein
   the link connector includes an air vent passage that allows the internal flow path to communicate with an external space further on a cannula side than the hemostasis valve, and
   a filter that allows gas to pass through but does not allow liquid to pass through is assembled in a compressed state on the air vent passage in which a radially inner surface of the filter is being pressed against a radially inner surface, while a radially outer surface of the filter is being pressed against a radially outer surface so that the filter is compressed between the radially inner surface and the radially outer surface which are radially opposite to each other.

2. The hemostasis valve-equipped indwelling needle according to claim 1, wherein
   the link connector includes a guide connector having a flow path constituting the internal flow path, and a connector cover into which a distal end portion of the guide connector is inserted and fixed, and
   a gap is provided between the guide connector and the connector cover such that the air vent passage includes the gap.

3. The hemostasis valve-equipped indwelling needle according to claim 1, wherein the filter is constituted by a material that allows gas to pass through but absorbs liquid.

4. An indwelling needle assembly comprising:
   the hemostasis valve-equipped indwelling needle according to claim 1; and
   a removable inner needle inserted from a proximal end side of the internal flow path toward a distal end side thereof.

5. A hemostasis valve-equipped indwelling needle comprising:
   an elastic valve body; and
   a pusher configured to move to a distal end side and be inserted into the elastic valve body such that the elastic valve body is pushed open, the pusher inserted into the elastic valve body being configured to be moved to a proximal end side due to a recovering action of the elastic valve body such that the elastic valve body is closed off, wherein
   an insertion region of the pusher into the elastic valve body includes a steep-inclined annular surface on an outer circumferential surface in an axially middle portion thereof, the steep-inclined annular surface having an inclination angle greater than that on a distal end side thereof, and
   in a state in which the elastic valve body is pushed and expanded by means of the pusher with the elastic valve body being held in contact with the steep-inclined annular surface, a pushing back force is exerted on the steep-inclined annular surface due to elastic recovery of the elastic valve body.

6. The hemostasis valve-equipped indwelling needle according to claim 5, wherein a distal end inclined surface having a tapered shape is provided on a distal end side of the steep-inclined annular surface.

7. The hemostasis valve-equipped indwelling needle according to claim 5, wherein a proximal end inclined surface having a tapered shape is provided on a proximal end side of the steep-inclined annular surface.

8. The hemostasis valve-equipped indwelling needle according to claim 5, wherein the steep-inclined annular surface has a tapered shape.

9. The hemostasis valve-equipped indwelling needle according to claim 5, wherein the inclination angle of the steep-inclined annular surface is constant.

10. The hemostasis valve-equipped indwelling needle according to claim 5, wherein
    a distal end inclined surface and a proximal end inclined surface each having a tapered shape are provided respectively on a distal end side and on a proximal end side of the steep-inclined annular surface, and
    inclination angles of the steep-inclined annular surface, the distal end inclined surface, and the proximal end inclined surface are all constant.

11. The hemostasis valve-equipped indwelling needle according to claim 5, further comprising
    a tubular housing that houses the elastic valve body and the pusher, wherein
    the pusher includes a contact part on an outer circumferential surface thereof further on a proximal end side than the insertion region,
    the tubular housing includes a locking protrusion on an inner circumferential surface thereof, and
    movement of the pusher to the proximal end side is restricted by contact of the contact part and the locking protrusion.

12. The hemostasis valve-equipped indwelling needle according to claim 5, wherein the inclination angle of the steep-inclined annular surface is set within a range of 25 to 75 degrees.

* * * * *